United States Patent
Giordani et al.

(10) Patent No.: US 8,372,866 B2
(45) Date of Patent: Feb. 12, 2013

(54) 2-ARYL AND 2-HETEROARYL 4H-1-BENZOPYRAN-4-ONE-6-AMIDINO DERIVATIVES, NEW PHARMACOLOGICAL AGENTS FOR THE TREATMENT OF ARTHRITIS, CANCER AND RELATED PAIN

(75) Inventors: Antonio Giordani, Pavia (IT); Ilario Verpilio, Arluno (IT); Stefania Mazza, legal representative, Arluno (IT); Sabrina Pucci, Lissone (IT); Roberto Artusi, Rho (IT); Gianfranco Caselli, Milan (IT); Marco Lanza, Lecco (IT); Laura Mennuni, Carnate (IT); Francesco Makovec, Lesmo (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 235 days.

(21) Appl. No.: 12/919,141

(22) PCT Filed: Mar. 6, 2008

(86) PCT No.: PCT/EP2008/052739
§ 371 (c)(1),
(2), (4) Date: Aug. 24, 2010

(87) PCT Pub. No.: WO2009/109230
PCT Pub. Date: Sep. 11, 2009

(65) Prior Publication Data
US 2011/0003861 A1    Jan. 6, 2011

(51) Int. Cl.
*A61K 31/4433* (2006.01)
*C07D 405/04* (2006.01)
(52) U.S. Cl. .................. 514/337; 546/283.1
(58) Field of Classification Search .............. 514/337; 546/283.1
See application file for complete search history.

(56) References Cited

FOREIGN PATENT DOCUMENTS
| | | |
|---|---|---|
| EP | 1 571 142 A1 | 9/2005 |
| WO | 00/12496 A1 | 3/2000 |
| WO | 02/24677 A1 | 3/2002 |

OTHER PUBLICATIONS

Goker, et al., "Synthesis and potent antimicrobial activity of some novel 2-phenyl or methyl-4H-1-benzopyran-4-ones carrying amidinobenzimidazoles," Bioorganic & Medicinal Chemistry, Mar. 2005, pp. 1707-1714, vol. 13, No. 5.
Cushman, et al., "Synthesis and Biochemical Evaluation of a Series of Aminoflavones as Potential Inhibitors of Protein-Tyrosine Kinases p56$^{ick}$, EGFr, and p60$^{v-src}$," J. Med. Chem, Jan. 1994, pp. 3353-3362, vol. 37, No. 20.
Purification and Cloning of Aggrecanase-1: A Member of the ADAMTS Family of Proteins; M.D. Tortorella, et al.; Science 284, 1664 (1999); DOI: 10. 1126/science.284.5420.1664.
Synthesis of 2,3,6,8-Tetrasubstituted Chromone Scaffolds; Kristian Dahlen, et al.; JOC Article; J. Org. Chem. 2006, 71, 6863-6871.
Novel Antiproliferative flavonoids induce cell cycle arrest in human prostate cancer cell lines; Haddad, et al.; Prostate Cancer and Prostatic Diseases (2006), 68-76.
A method for Measurement of Analgesic Activity on Inflamed Tissue; Lowell Randall and Joseph Selitto, Arch. Inc. Pharacodyn, 1957, CX1. No. 4.
Risk assessment of NSAID-induced gastrointestinal toxicity in ambulatory care patients; Burgunda V. Sweet, et al.; Am j Health-Syst Pharm—vol. 61, Sep. 15, 2004.
Synthesis and potent antimicrobial activity of some novel 2-phenyl or methyl-4H-1-benzopyran-4-ones cary amidinobenzimidazoles; Goker, et al.; Bioorganic & Medicinal Chemistry; 2005 1707-1714.
Cytokines, nerve growth factor and inflammatory hyperalgesia: the contribution of tumour necrosis factor; British Jouran of Pharmacology (1997) 121, 417-424.
Streptozocin-induced diabetic rats: behavioural evidence for a model of chronic pain; C. Courteix, et al.; Pain, 53 (1993) 81-88.
In Vivo Osteoarthritis Target Validation Utilizing Genetically-Modified Mice; Glasson; Crrent Drug Targets, 2007, 8, 367-376.
Review: ADAMTS proteinases: a multi-domain, multi-functional family with roles in extracellular matrix turnover and arthritis; Jones, et al.; Arthritis Research & Therapy, Aug. 2005, vol. 7, No. 4, Jones, et al.
REview Article. The ADAMTS metalloproteinases; Porter, et al.; Biochem. J. (2005) 386, 15-27.
Antispasmodics and Antihistmainics Derived From Amino Flavones; P.K. Jesthi and Y. Behera; J. Inst. Chemists (India), vol. 53, Sep. 1982; pp. 234-236.
Syntheses of 5,7,8- and 5,6,7-Trioxygenated 3-Alkyl-3',4'-dihydroxyflavones and Their Inhibitory Activites against Arachidonate 5-Lipoxygenase; Horie, et al.; J. Med. Chem. 1991, 34, 2169-2176.
Synthesis of Kaempferitrin, Sameer Urgankar and Jared T. Shaw, JOC Note; J. Org. Chem. 2007, 72, 4582-4585. Cyclo-oxygenase-2 Inhibitors versus Non-selective non-steroidal anti-inflammatory drugs and congestive heart failure outcomes in elderly patients: a population-based cohort study, Muhammad Mamdani, et al.; Articles; The Lancet, vol. 363, May 29, 2004; 1751-1756.
Animal Models for Pain Research, Katharine Walker, Alyson J. Fox and Laszio A. Urgan, Disease Models; Molecular Medicine Today, Jul. 1999, vol. 5, pp. 319-321.
Remodelling of Spinal Nociceptive Mechansims in an Animal Model of Monoarthritis, Reza Sharif Naeini, et al.; European Journal of Neuroscience, vol. 22, pp. 2005-2015, 2005.

(Continued)

*Primary Examiner* — Taofiq A Solola
(74) *Attorney, Agent, or Firm* — Sughrue Mion, PLLC

(57) ABSTRACT

2-aryl and 2-heteroaryl 4h-1-benzopyran-4-one-6-amidino derivatives formula (I)

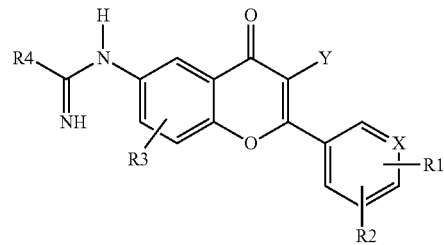

useful as pharmacological agents for the treatment of arthritis, cancer and related pain.

18 Claims, No Drawings

OTHER PUBLICATIONS

A New General Method for the Synthesis of The Derivatives of Flavolon, T. Oyamada, vol. 10, Translation from the original J. Chem. Soc. Japan 55 (1934), 1256, pp. 182-186.

TSRI MLSCN Probe Report for Inhibitors of ADAMTS-4: Piceatannol, The Scripps Research Institute Molecular Screening Center, Hugh Rosen, Sep. 15, 2007.

4'-Hydroxy-3-methoxyflavones with Potent Antipipcornavirus Activity; De Meyer, et al.; J. Med. Chem. 1991, 34, 736-746.

Imidazol-1-yl and Pyridin-3-yl Derivatives of 4-Phenyl-1,4-dihydropyridines Combining Ca2+ Antagonism and Thromboxand A2 Synthase Inhibition; Cozzi, et al.; J. Med. Chem. 1993, 36, 2964-2972.

Synthesis and Biochemical Evaluation of a Series of Aminoflavones as Potential Inhibitors of Protein-Tyrosine Kinases p 56 Ick, EGFr, and p60 v-arc; Cushman, et al.; J. Med. Chem. 1994, 37, 3353-3362.

Effects of Flavonoids on Cell Proliferation and Caspase Activation in a Human Colonic Cell Line Ht29; An SAR Study; J. Med. Chem 2005, 48, 2790-2804.

Synthesis of Some New 6-amino-3-methoxyflavones; Palkar, et al.; Indian Journal of Chemistry; vol. 39B, Feb. 2000, pp. 141-144.

Synthesis of 6-Amino-2-Aryl-4H-1-Benzopyran-4-Ones; Palkar, et al.; Indian Journal of Heterocyclic Chemistry, vol. 7, Jul.-Sep. 1997, pp. 25-30.

Generation and Characterization of Aggrecanase, A Soluble, Cartilage-Drived Aggrecan-Degrading Activity; Arner, et al.; The Journal of Biological Chemistry, vol. 274, No. 10, Issue of Mar. 5, 1999, pp. 6594-6601.

A Quantitative Assay for Aggrecanase Activity; Horst Will, et al.; Journal of Biomolecular Techniques, vol. 16, Issue 4, Dec. 2005, pp. 459-472.

The Structure of Aggrecan Fragments in Human Synovial Fluid Evidence for the Involvement in Osteoarthritis of a Novel Proteinase Which Cleaves the Glu 373-Ala 374 Bond of the Interglobular Domain, John D. Sandy, et al.; J. Clin. Invest. The American Society for Clinical Investigation, Inc., vol. 89, May 1992, 1512-1516.

Antispasmodics and Antihistaminics Derived from Amino Flavones; Jesthi and Behera; J. Inst. Chemists (India), vol. 53, Sep. 1981.

Meller, S. T. et al., "The Possible Role of Glia in Nociceptive Processing and Hyperalgesia in the Spinal Cord of the Rat", Department of Pharmacology, University of Iowa, Jun. 21, 1994, Iowa City.

Roughley, P.J. "The Structure and Function of Cartilage Proteoglycans", European Cells .and Materials, vol. 12. 2006, pp. 92-101.

2-ARYL AND 2-HETEROARYL 4H-1-BENZOPYRAN-4-ONE-6-AMIDINO DERIVATIVES, NEW PHARMACOLOGICAL AGENTS FOR THE TREATMENT OF ARTHRITIS, CANCER AND RELATED PAIN

CROSS REFERENCE TO RELATED APPLICATIONS

This application is a National Stage of International Application No. PCT/EP2008/052739 filed Mar. 6, 2008 the contents of all of which are incorporated herein by reference in their entirety.

The present invention is directed to novel 2-aryl and 2-heteroaryl-4H-1-benzopyran-4-one-6-amidino derivatives, to their pharmaceutically acceptable salts, to a process for their preparation, to their pharmaceutical compositions and to the use of such compounds and their pharmaceutical compositions for the treatment of arthritis, pain and cancer.

BACKGROUND OF THE INVENTION

Osteoarthritis (OA) is a progressive degenerative joint disease which affects a large part of the elderly population seriously impacting the quality of life. OA is characterised by pathological changes that occur in the articular cartilage, synovium and subchondral bone leading to pain and loss of articular function. Rheumatoid arthritis (RA) is a systemic inflammatory disease characterised by articular synovitis leading to cartilage degradation, bone erosion and pain. Although arthritis (OA and RA) are defined as a diseases affecting the joints, the primary feature is chronic pain. Accordingly, the most of the currently used pharmacological treatment for arthritis is largely confined to analgesics, steroidal and especially non-steroidal anti-inflammatory drugs (NSAIDs). These agents impact the symptoms of the disease (mainly pain) rather than the underlying process, in addition, though these drugs have provided an important mean of controlling inflammation and pain in arthritis, their application has been overshadowed by the gastrointestinal tract side-effects, when considering classical NSAIDs drugs (By Sweet et al., Am. J. Health Syst. Pharm., 61, 18, 1917-21, 2004) and other side-effects when considering COX-2 inhibitors (Mamdani M. et al., Lancet, 363, 1751-6, 2004). Therefore, the development of new therapeutic agents able to prevent or counteract cartilage degradation in arthritis along with the related pain is essential, since OA and RA affect million people all over the world and its incidence is expected to increase with the increase of the population average age.

The degradation of cartilage that occurs in these diseases is the result of enzymatic cleavage of its structural components. Cartilage is constituted of chondrocytes and an extra-cellular matrix that consists of proteoglycans (mainly aggrecan), collagen and water. The interaction between proteoglycans and collagen provides unique structural and physiological properties for cartilage to function in weight bearing and joint motion. Cartilage proteoglycans consist of a protein core with glycosaminoglycan (GAG) side chains; GAG components absorb water and provide to the cartilage its characteristic resistance to mechanical stress and constitute a protective layer essential to the joint function. Healthy cartilage maintains a dynamic equilibrium between processes that produce and processes that degrade the matrix components; in pathological conditions this equilibrium is altered leading to the prevalence of the degenerative process, which causes matrix degradation, and hence cartilage roughening and fissuring which at the end could result in erosion of the subchondral bone and synovial inflammation.

The large aggregating proteoglycan, called aggrecan, forms aggregates that bind hyaluronic acid (HA) and together with type II collagen is responsible for the biomechanical properties of cartilage. Thus aggrecan interacting in a complex network with HA and type II collagen, enables the tissue to bear load resisting to mechanical compression and endows the cartilage with those biomechanical characteristics necessary to joint functionality. Aggrecan protein consists of three globular regions termed G1, G2 and G3 (P. J. Roughley, European Cells & Material, 2006, 12, 92-101). The G1 and G2 regions are separated by a short interglobular domain (IGD) while the G2 and G3 regions are separated by a long GAG attachment region. The G1 domain is at the amino-terminus of the protein and through an ancillary protein it constitutes the binding region of aggrecan to HA. Aggrecan molecules are not isolated within the extra-cellular matrix but form aggregates composed of a central HA filament with up to 100 aggrecan molecules radiating from it. The GAG-attachment region of aggrecan provides the high anionic charge density needed for binding water and conferring to the cartilage the unique osmotic properties necessary to guarantee its functionality.

Loss of cartilage integrity in arthritis is associated with impaired aggrecan integrity due to proteolytic cleavage of the protein. Two sites located in the IGD of aggrecan have been identified as the major targets of proteolytic aggrecan attack the $Asn^{341}$-$Phe^{342}$ bond has been shown to be mainly cleaved by several Matrix Metalloproteases (MMPs) and the $Glu^{373}$-$Ala^{374}$ bond which is the site of cleavage in pathological conditions as resulted by analysis of synovial fluids of patients (L. S. Lohmander et al., Arthritis & Rheum., 1993, 36, 1214-1222; J. D. Sandy, J. Clin. Invest. 1992, 89, 1412. B) or in widely reported laboratory studies, where this site resulted the major aggrecan cleavage site in chondrocytes cultures stimulated by cytokines (the cytokines: IL-1, TNF-α, IL-6, IL-8 stimulate the chondrocytes to produce an increased amount of matrix degrading enzymes, while IL-4 inhibits this process). Two enzymes, Aggrecanase 1 and 2, which cleave aggrecan at $Glu^{373}$-$Ala^{374}$ bond but not at the MMP site, have been identified and cloned. Both these enzymes belong to the ADAMTS (a disintegrin-like and metalloproteinase domain with thrombospondin type 1 motifs) family of proteases and are named ADAMTS-4 and ADAMTS-5 respectively. ADAMTS family represents a group of zinc metalloproteases belonging to reprolysin subfamily (related to the snake venom toxin reprolysin; C. G. Jones et al., Arthritis Res. Ther, 2005, 7, 160-69; C. G. Jones et al., Biochem J., 2005, 386, 15-27).

While enzymes in ADAMTS family are usually involved in protein turnover and tissue remodelling, ADAMTS-4 and ADAMTS-5 are considered to be largely responsible for the cartilage aggrecan catabolism observed during the development of OA and RA, therefore inhibition of these enzymes may represent a therapeutic strategy for these diseases (S. S. Glasson, Current Drug Targets, 2007, 8, 2, 367-376). Though synthetic MMPs inhibitors have been clinically investigated as a means to block tissue destruction in arthritis and have been proved unsuccessful, it should be pointed out that these inhibitors were directed against MMPs which cleaves mainly collagen and interact for a minor extent with aggrecan. Conversely, aggrecanases which cleaves with high efficiency aggrecan within the IGD site, give rise to the removal of a large part of the protein from its binding site to HA thus leading to the breakage of that complex network of interactions fundamental to cartilage integrity and functions.

In addition, several members of the ADAMTS family including ADAMTS-4 and ADAMTS-5 have been found over-expressed in tumour cell lines. It should be pointed out that a prerequisite for invasiveness in cancer is cell migration based on increased expression of proteases digesting the extra-cellular matrix, the same process of extra-cellular matrix remodelling mediated by metalloproteases is also essential in angiogenesis, the process by which new blood vessels are formed from pre-existing vasculature. Angiogenesis has also been identified as a contributing factor in cancer where it is a rate-limiting step during tumour progression. Accordingly, in addition to arthritis ADAMT-4/-5 inhibitors could be useful therapeutic agents for the treatment of cancer.

The 2-phenyl-4H-1-benzopyran-4-one nucleus is well known in nature, since flavonoids form a class of benzopyran-4-one derivatives which are ubiquitous in plants as secondary metabolites. Flavonoids such as flavones and flavonols are present in a great variety of food, and especially in fruits and vegetables. Among them, Quercetin [2-(3,4-dihydroxyphenyl)-3,5,7-hydroxy-4H-1-benzopyran-4-one)] is the main flavonoid occurring in the food and is present at an average level of 10 mg/Kg (in onion its concentration is 300 mg/kg). Quercetin is a very effective antioxidant and appeared to be active in treating several disease such as cardiovascular, neurodegenerative and cancer. Further investigations highlighted how the proprieties of the 4H-1-benzopyran-4-one scaffold also known as chromenone, are not confined to Quercetin only but can be efficiently used as structural scaffolds for drug design.

Several 6-amino-2-aryl-4H-1-benzopyran-4-one derivatives are known in literature: 6-amino-2-phenyl-4H-1-Benzopyran-4-one (RN: 4613-53-0) has been reported along with other 26 flavonoids as anti-proliferative agents acting on cell cycle (Haddad, A. Q.; Prostate Cancer and Prostatic Diseases (2006), 9(1), 68-76), antispasmodic and antihistaminic activity has been reported for another group of 2-aryl-6-amino-chromen-4-one derivatives (P. K. Jesthi et al., Journal of the Institution of Chemists (India) (1981), 53(5), 234-6), inhibition of several protein kinases was reported for a group of aminoflavones (M. Cushman et al, Journal of Medicinal Chemistry (1994), 37(20), 3353-62), as well as inhibition of CDK kinase for a wide group of flavonoids including amino derivatives (PCT Int. Appl. (2000), WO 2000012496 A1 20000309). N-carbamoylderivatives of a group of aminoflavones have been reported as acetylcholine esterase inhibitors (PCT Int. Appl. (2002), WO 2002024677 A1 20020328). Though an amidine of a flavanone derivative has been reported as furamidine analogue (RN: 849368-08-7,2-[4-[amino[(1-methylethyl)imino]methyl]phenyl]-N-(1-methylethyl)-4H-1-Benzopyran-4-oxo-6-carboximidamide, H Goeker et al., Bioorganic & Medicinal Chemistry, 2005, 13(5), 1707-1714), exhibiting antimicrobial activity, none of these flavanone amino or amidinoderivatives has never been reported neither as aggrecanase inhibitor nor as analgesic.

SUMMARY OF THE INVENTION

The present invention comprises a new class of compounds, 2-aryl and 2-heteroaryl-4H-1-benzopyran-4-one-6-amidino derivatives of formula (I) and pharmaceutically acceptable salts thereof, useful for the pharmacological treatment of diseases such as traumatic joint injuries, arthritis, typically osteoarthritis, rheumatoid arthritis and psoriatic arthritis, cancer including but not limited to brain tumours, in particular glioblastoma, colon cancer, multiple myeloma, breast, cervical, prostate and lung cancer. In addition, compounds of the invention are potent analgesics, independently upon the pain was inflammatory pain or neuropathic pain. Accordingly, the compounds of the invention are useful for the treatment of acute and chronic pain, such as: osteoarthritis and rheumatoid arthritis pain, postoperative pain, visceral pain, pain associated with cancer, trigeminal neuralgia, acute herpetic and post herpetic neuralgia, diabetic neuropathy acute and chronic pain, postoperative pain, muscular pain, pain resulting from various forms of trauma, visceral pain.

Compounds of formula (I):

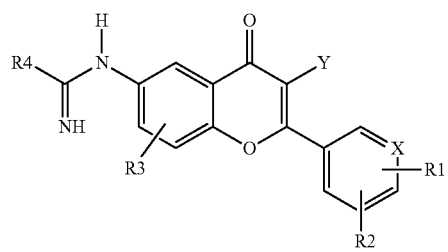

where:
X is independently selected between a (—CH—) group or a nitrogen atom (—N—). When X is the (—CH—) group, the aromatic group in position -2 of the 4H-1-benzopyran-4-one nucleus is a phenyl or a substituted phenyl, when X is nitrogen the aromatic group in position -2 of the 4H-1-benzopyran-4-one moiety is a 3-pyridyl group;

Y is independently selected from an hydrogen atom (—H), an hydroxy group (—OH), an alkoxy group (—OR), where R is a $C_1$-$C_4$ linear or branched alkyl chain, or a —OCH$_2$OCH$_3$ group (oxy-methoxymethyl group), or a group —O—CH$_2$COOH (2-oxyacetate group) or a group —O—CH$_2$COONH$_2$, or a group —O—CH$_2$—COOR where R is as defined above, or an alkyl group (—R), where R is as defined above;

$R_1$ and $R_2$ are independently substituents in the ortho, meta and para positions of the phenyl ring or are independently substituents of the positions: -2, -4, -5 and -6 of the pyridine ring. $R_1$ and $R_2$ substituents are independently selected from: hydrogen (—H), fluorine (—F), chlorine (—Cl), bromine (—Br), $C_1$-$C_4$ linear or branched alkyl chain (—R), trifluoromethyl (—CF$_3$), cyano (—CN), methansulfonyl (—SO$_2$CH$_3$), methansulfonamido (—NHSO$_2$CH$_3$), sulfonamido (—SO$_2$NH$_2$), alkoxy (—OR) where R is as defined above, trifluoromethoxy (—OCF$_3$), benzyloxy (—OCH$_2$Ph);

$R_1$ can be a penta-atomic heterocyclic group, preferably selected from: 1H-1-imidazolyl, 1H-2-methyl-1-imidazolyl, 1H-4-methyl-1-imidazolyl, 1H-5-methyl-1-imidazolyl, imidazol-2-yl, 1-methyl-imidazol-2-yl, oxazol-2-yl, or a group methyl-1H-imidazol-1-yl (—CH$_2$-1H-imidazol-1yl). When the $R_1$ group is a penta-atomic heterocycle as defined above, it can be in position -3 or -4 of the phenyl, or in position -2 and -6 of the pyridine moiety, $R_2$ is as defined above;

when $R_1$ and $R_2$ substituents are in position -3 and -4 of the phenyl, they can optionally form a 5 or 6 member heterocyclic ring condensed with the aryl moiety, said ring being preferably a dioxolane, a furane, a 2,3-dihydrofurane or a 1H-3,4-tetrahydropyrane moiety; in these cases, the aromatic group in position -2 of the 4H-1-benzopyrane nucleus will be respectively a 1,3-benzodiozol-5-yl group, a benzofuran-5-yl- or benzofuran-6- yl group, a 2,3-dihydrobenzofuran-5-yl or 2,3-dihydrobenzofuran-6-yl group, a 2,3-dihydro-1,4-benzodioxin-6-yl group;

$R_3$ is in position −5, −7 or −8 of the 4H-1-benzopyran-4-one nucleus, it is selected from: hydrogen (—H), fluorine (—F), a $C_1$-$C_4$ linear or branched alkyl chain (—R), hydroxy (—OH) methoxy (—OCH$_3$), trifluoromethoxy (—OCF$_3$), carboxy (—COOH), carboalkoxy (—COOR), being R as defined above, carboxamido (—CONH$_2$), carboxymethyl (—CH$_2$COOH), carboalkoxymethyl (—CH$_2$COOR), carboxamidomethyl (—CH$_2$CONH$_2$), dimethylaminomethyl (—CH$_2$NMe$_2$), being R as defined above;

the amidino group: $R_4$—C(=NH)—NH—, is in position −6 of the 4H-1-benzopyran-4-one nucleus, $R_4$ is independently selected from a cyclopropyl (—C$_3$H$_5$), a cyclopropylmethyl (—CH$_2$C$_3$H$_5$), a $C_1$-$C_4$ linear or branched alkyl chain (—R), optionally substituted with an hydroxy group (—OH), a methoxy group (—OCH$_3$), an ethoxy group (-OC$_2$H$_5$) or a dimethylamino group (—NMe$_2$), a phenyl or a substituted phenyl, where for substituted phenyl is intended a phenyl substituted with at least one of the following groups: fluorine (—F), chlorine (—Cl), bromine (—Br), methoxy (—OCH$_3$) and 3,4-methylendioxy (—O—CH$_2$—O—); in addition, $R_4$ can be a phenyl or a substituted phenyl as defined above or an heterocycle such as—2-furyl, 3-furyl, 2-thienyl, 3-thienyl, 2-oxazolyl, 3-oxazolyl, 2-thiazolyl, 3-thiazolyl.

In compounds of Formula (I) the amidine substituent can give rise to tautomers, the scope of the present invention includes all the possible tautomers of compounds of formula (I).

According to this invention the compounds of Formula (I) may be used as the free base or as a pharmaceutically acceptable salt thereof, or as a solvate or hydrate form of such salt.

The salts of the compounds of Formula (I) are pharmaceutically acceptable addition salts with inorganic and organic acids. Representative not limiting examples of inorganic salts are: hydrochloride, hydrobromide, hydrogensulphate and sulphate. Representative not limiting examples of organic salts are: maleate, fumarate, oxalate, methanesulphonate, succinate, ascorbate, tartrate.

In another embodiment this invention provides methods for the preparation of compounds of Formula (I).

In a further embodiment this invention provides pharmaceutical compositions for compounds of Formula (I), useful for the treatment of arthritis, cancer and pain as discussed above. Within the scope of the present invention the term pharmaceutical composition (drug product) refers to any oral, parenteral or topical dosage form, suitable for the treatment of the above pathologies, that contains an effective amount of at least one of the active pharmaceutical ingredients (drug substances), compounds of Formula (I), its salts or solvates thereof, and a pharmaceutically acceptable carrier, excipients or diluents as defined below, for oral, parenteral or topic administration.

Representative not limiting examples of compounds of Formula (I) are listed in the Table 1.

TABLE 1

| Example | Structure | Molecular Formula | Molecular Weight |
|---|---|---|---|
| 1 | 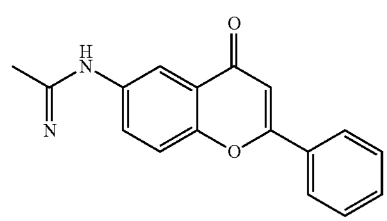 [SMILES: CC(=N)Nc1ccc2oc(-c3ccccc3)cc(=O)c2c1] | C17H14N2O2•HCl | 314.8 |
| 2 | 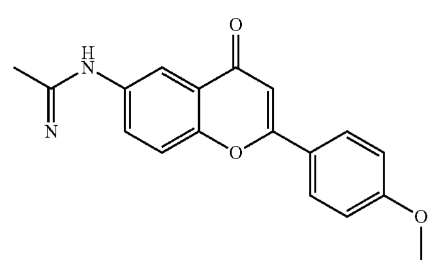 | C18H17N2O3•HCl•H2O | 363.9 |
| 3 | 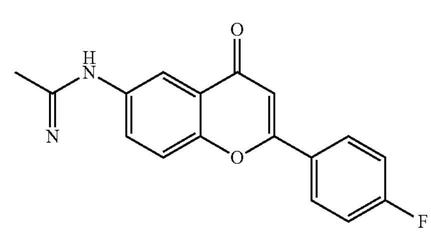 [SMILES: CC(=N)Nc1ccc2oc(-c3ccc(F)cc3)cc(=O)c2c1] | C17H13FN2O2 | 296.3 |

TABLE 1-continued

| Example | Structure | Molecular Formula | Molecular Weight |
|---|---|---|---|
| 4 | 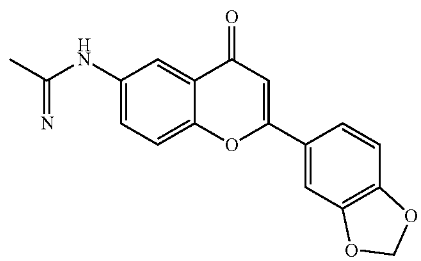 [SMILES: CC(=N)Nc1ccc2oc(-c3ccc4c(c3)OCO4)cc(=O)c2c1] | C18H14N2O4•HCl | 358.7 |
| 5 | 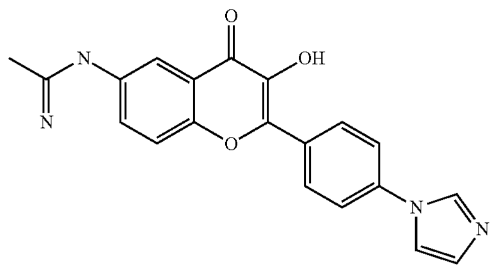 [SMILES: CC(=N)Nc1ccc2oc(-c3ccc(-n4ccnc4)cc3)c(O)c(=O)c2c1] | C20H16N4O3•HCl | 396.9 |
| 6 | 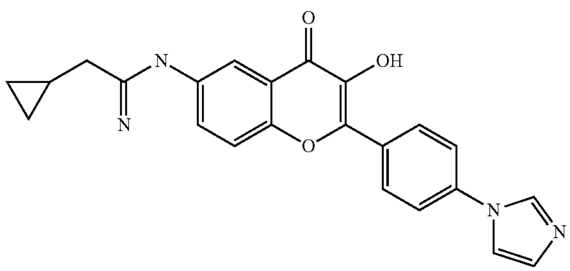 [SMILES: N=C(CC1CC1)Nc1ccc2oc(-c3ccc(-n4ccnc4)cc3)c(O)c(=O)c2c1] | C23H20N4O3•2HCl•H2O | 491.4 |
| 7 | 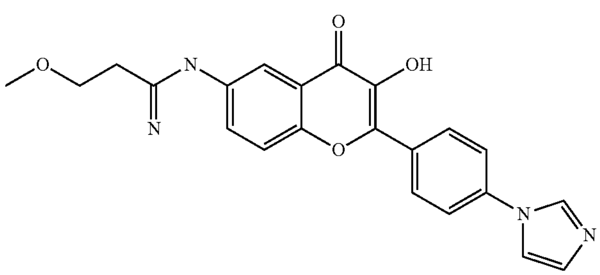 [SMILES: COCCC(=N)Nc1ccc2oc(-c3ccc(-n4ccnc4)cc3)c(O)c(=O)c2c1] | C22H20N4O4 | 404.4 |
| 8 | 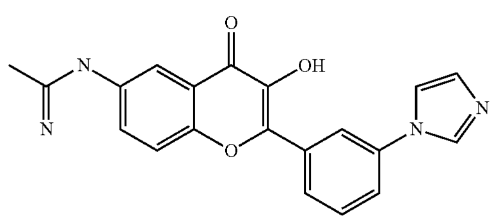 [SMILES: CC(=N)Nc1ccc2oc(-c3cccc(-n4ccnc4)c3)c(O)c(=O)c2c1] | C20H16N4O3•2HCl | 396.9 |
| 9 | 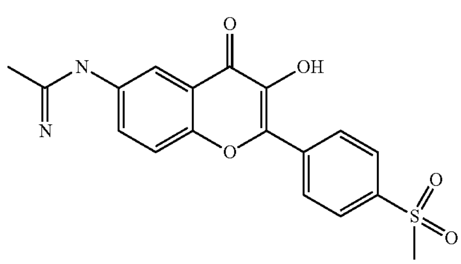 [SMILES: CC(=N)Nc1ccc2oc(-c3ccc(S(C)(=O)=O)cc3)c(O)c(=O)c2c1] | C18H16N2O5S•HCl | 408.9 |

TABLE 1-continued

| Example | Structure | Molecular Formula | Molecular Weight |
|---------|-----------|-------------------|------------------|
| 10 | 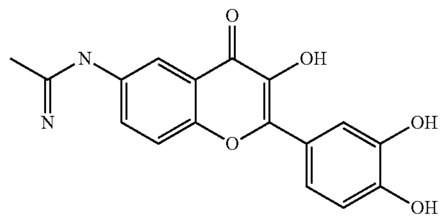 [SMILES: CC(=N)Nc1ccc2oc(-c3ccc(O)c(O)c3)c(O)c(=O)c2c1] | C17H14N2O5•HCl | 362.8 |
| 11 | 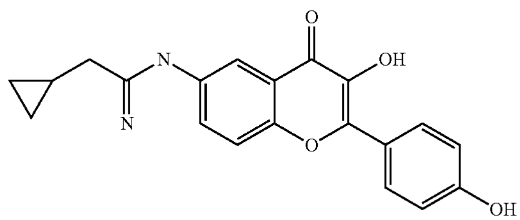 [SMILES: N=C(CC1CC1)Nc1ccc2oc(-c3ccc(O)cc3)c(O)c(=O)c2c1] | C20H18N2O4•HCl | 386.9 |
| 12 | 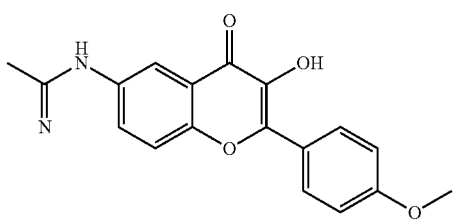 [SMILES: COc1ccc(-c2oc3ccc(NC(C)=N)cc3c(=O)c2O)cc1] | C18H17N2O4•HCl•H2O | 325.4 |
| 13 | 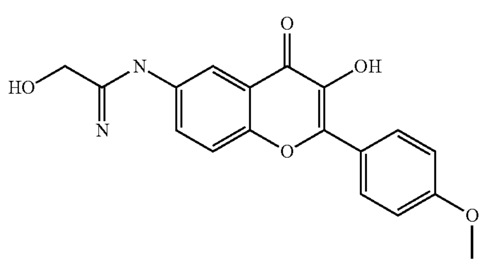 [SMILES: COc1ccc(-c2oc3ccc(NC(=N)CO)cc3c(=O)c2O)cc1] | C18H16N2O5•HCl•H2O | 434.4 |
| 14 | 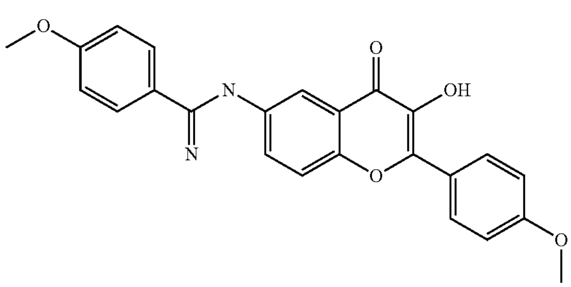 | C24H20N2O5•HCl | 452.9 |
| 15 | 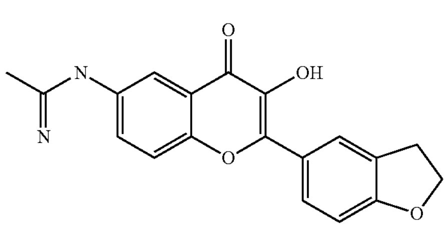 | C19H16N2O4•HCl | 372.8 |

TABLE 1-continued

| Example | Structure | Molecular Formula | Molecular Weight |
|---|---|---|---|
| 16 | 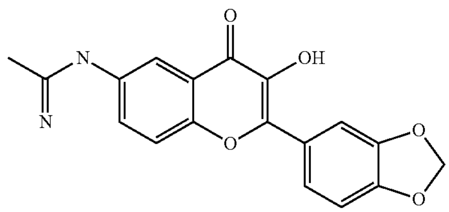 | C18H14N2O5•HCl | 374.8 |
| 17 | 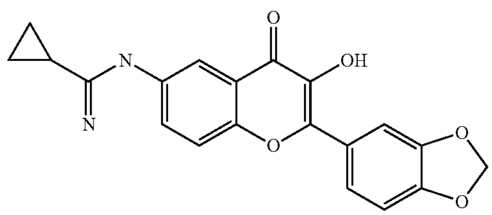 [SMILES: N=C(Nc1ccc2oc(-c3ccc4c(c3)OCO4)c(O)c(=O)c2c1)C1CC1] | C20H16N2O5 | 364.4 |
| 18 | 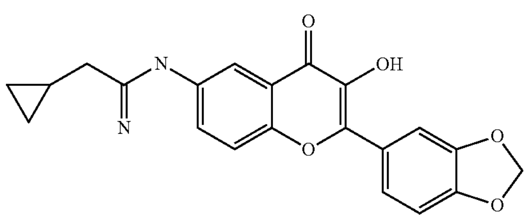 [SMILES: N=C(CC1CC1)Nc1ccc2oc(-c3ccc4c(c3)OCO4)c(O)c(=O)c2c1] | C21H18N2O5•HCl | 414.9 |
| 19 | 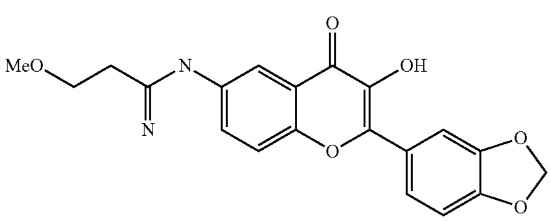 [SMILES: COCCC(=N)Nc1ccc2oc(-c3ccc4c(c3)OCO4)c(O)c(=O)c2c1] | C20H18N2O6 | 382.4 |
| 20 | 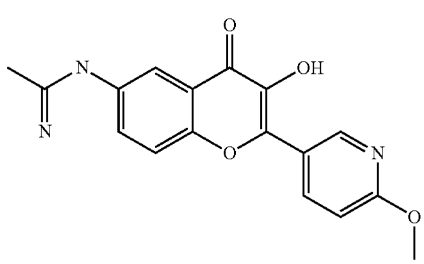 [SMILES: COc1ccc(-c2oc3ccc(NC(C)=N)cc3c(=O)c2O)cn1] | C17H15N3O4•HCl | 361.8 |
| 21 | 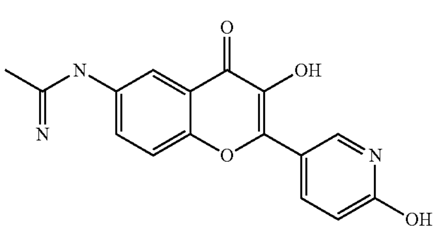 [SMILES: CC(=N)Nc1ccc2oc(-c3ccc(O)nc3)c(O)c(=O)c2c1] | C16H13N3O4•HCl | 347.8 |

TABLE 1-continued

| Example | Structure | Molecular Formula | Molecular Weight |
|---|---|---|---|
| 22 | 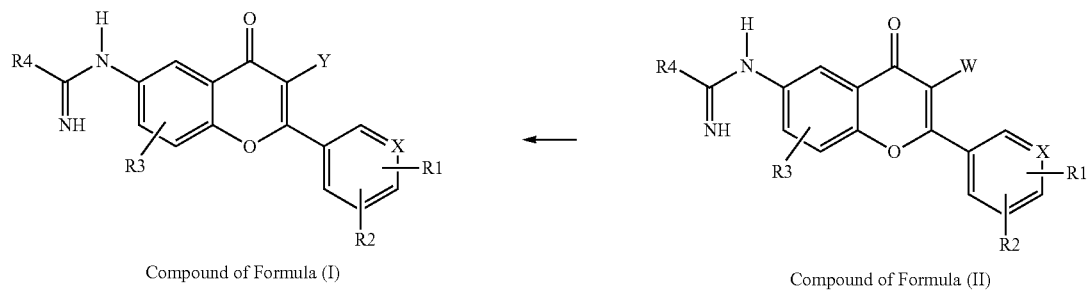 | C25H23N2O4•HCl | 415.5 |

DESCRIPTION OF THE INVENTION

Preparation of the Compounds of the Invention

Compounds of Formula (I) can be prepared from compounds of Formula (II):

Compound of Formula (I) ← Compound of Formula (II)

wherein in compounds of Formula (II) the substituents X, $R_1$, $R_2$, $R_3$, $R_4$ have the same meanings as previously reported for compounds of formula (I) and the substituent W in addition to the meanings previously reported for compounds of formula (I) can be a benzyloxy group (—OCH$_2$Ph), or a silyloxy group, typically trimethylsilyloxy (—OSiMe$_3$) and tertbutyldimethylsilyloxy group (—OSiMe$_2$tBut). Conversion of a compound of formula (II) into a compound of formula (I) where Y is hydroxy, can be obtained when W is a benzyloxy group, for example by catalytic hydrogenation (J. Med. Chem., 48, 8, 2790-2804; 2005), when W is a methoxymethyl group by acidic treatment and by treatment with tetrabutylammonium fluoride in THF or with aqueous acid such as aqueous hydrochloric acid when W is a silyloxy group.

A compound of formula (II) where $R_1$ and/or $R_2$ are alkoxy groups can be transformed into a compound of formula (I) where $R_1$ and/or $R_2$ are hydroxy groups, using techniques well known in the art, for example by treatment with aqueous hydrochloric or hydrobromic acid or aluminium tribromide or boron tribromide (J. Org. Chem. 72, 12, 4582-4585; 2007).

A compound of formula (II) where $R_1$ and/or $R_2$ are benzyloxy groups can be transformed into a compound of formula (I) where $R_1$ and/or $R_2$ are hydroxy groups by catalytical hydrogenation. A compound of formula (II) where $R_3$ and/or Y is a carboalkoxy containing group can be transformed into a compound of formula (I) where $R_3$ and/or Y is a carboxy group. In this case if the alkoxy group is methoxy or ethoxy the transformation can be obtained by treatment with aqueous or alcoholic sodium or potassium hydroxide if the alkoxygroup is tertbutoxy its removal can be achieved by treatment with trifluoroacetic acid in a suitable solvent such as dichloromethane. A compound of formula (II) where $R_3$ and/or Y is a carboalkoxy containing group can be transformed into a compound of formula (I) where $R_3$ and/or Y is a carboxamido group by reaction of the ester with ammonia or by ester hydrolysis as described above and then for example by treatment of the resulting acid with oxalyl chloride followed by treatment of the resulting acylchloride with ammonia.

A compound of formula (II) can be obtained from a compound of formula (III):

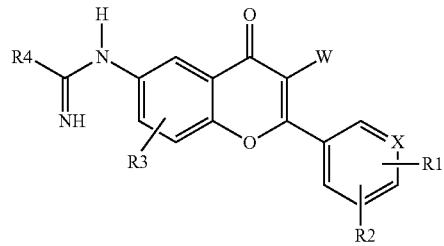

Compound of Formula (II)

wherein in compounds of formula (III) the substituents X, $R_1$, $R_2$, $R_3$, $R_4$, and W have the same meanings as previously reported for compounds of formula (II). Conversion of a compound of formula (III) into a compound of formula (II) can be obtained by treatment with $R_4CN$ and an appropriate catalyst, in a suitable inert solvent such as dioxane, tetrahydrofurane (THF), diglyme, hexane or toluene, or using the cyanide as solvent. Appropriate catalysts can be: trimethylaluminium in hydrocarbon solvents such as hexane or toluene, dry hydrochloric acid or methansulphonic acid. Alternatively, conversion of a compound of formula (III) into a compound of formula (II) can be obtained by treatment with an imidate of formula $R_4C(=N)$—OR, where $R_4$ is as defined for compounds of formula (I) and R is ethyl or methyl. The reaction is usually carried out in a suitable solvent such as methanol or ethanol at a temperature that can vary from 25° C. to the reflux temperature. Since the imidate is usually as hydrochloride salt an organic base such as triethylamine or N-methylmorpholine is used as well.

A compound of formula (I) can be directly obtained from a compound of formula (III) using the above methods provided that Y, W, $R_1$, $R_2$, $R_3$, $R_4$ are appropriate with the method used for the direct conversion of a compound of formula (III) into a compound of formula (I).

A compound of formula (III) can be obtained from a compound of formula (IV):

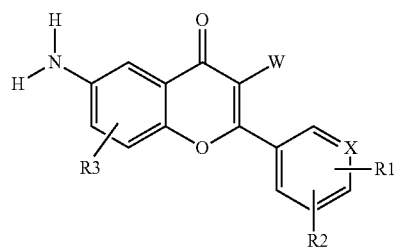

Compound of Formula (III)

wherein in compounds of formula (III) all the substituents are as previously defined and PG is an appropriate nitrogen protecting group. Appropriate protecting groups being amides, for example acetyl (—COCH$_3$) and trifluoroacetyl (—COCF$_3$) and carbamates for example BOC: tertbutoxycarbonyl (—COOtBut). Conversion of compounds of formula (IV) into compounds of formula (III) is obtained according to methods well know in the art (T. W. Green, Protective group in Organic Synthesis, John Wiley & Sons). A compound of formula (IV) where W is hydroxyl can be transformed into a compound of formula (IV) where W is a group —O—CH$_2$COOH (2-oxyacetate group) or a group —O—CH$_2$COONH$_2$, or a group —O—CH$_2$—COOR where R is as defined above, by treatment of the compound of formula (IV) with either ethyl bromoacetate or tertbutylbromoacetate and sodium or potassium carbonate in a suitable solvent such as DMF (J. Org. Chem., 71, 18, 6863-6871; 2006). A compound of formula (IV) wherein Y is group —O—CH$_2$COONH$_2$ can be obtained from a compound of formula (IV) wherein Y is group —O—CH$_2$—COOR or a group —O—CH$_2$COOH according to methods well know in the art.

A compound of formula (IV) can be obtained from a compound of formula (V) by reaction with a compound of formula (VI) wherein substituents are as defined above and Z is selected from a carboxylate group (—COOH) or a group —CO—$R_5$ where $R_5$ is a $C_1$-$C_4$ linear or branched alkyl chain, a methoxymethyl group (CH$_2$OCH$_3$) or hydrogen (—H):

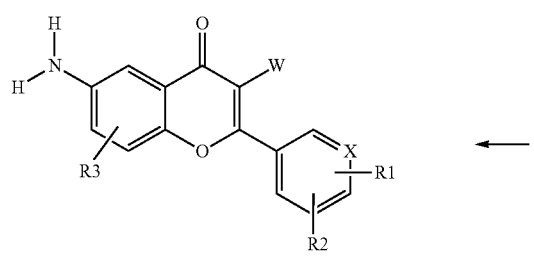

Compound of Formula (III)

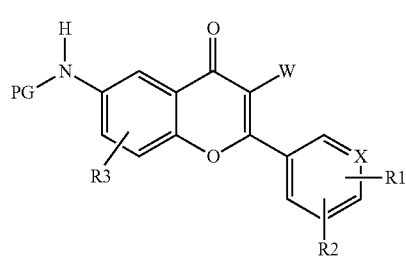

Compound of Formula (IV)

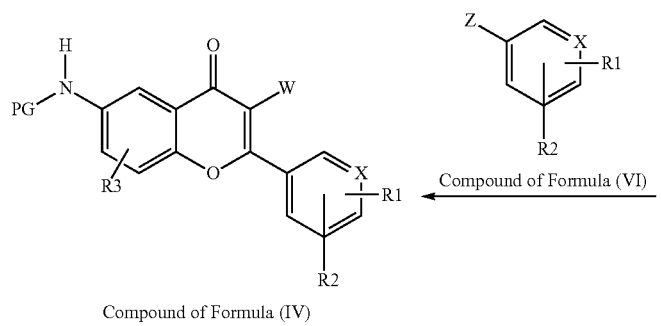
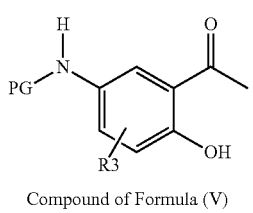

Compound of Formula (IV)   Compound of Formula (VI)   Compound of Formula (V)

Compounds of formula (V) and compounds of formula (VI) are commercially available or can be prepared according to known routes.

Synthesis of compounds of formula (IV) from compounds of formula (V), when W is hydrogen (—H) is obtained by esterification of the compound of formula (V) with substituted aromatic acids of formula (VI) (Z: COOH) to provide 2-aryloxyacetophenones, which on Baker-Venkataraman rearrangement gave the corresponding 1,3-diketones. Compounds of formula (IV) are then obtained by cyclodehydration of 1,3-diketones. Esterification and Baker-Venkataraman rearrangement can be obtained using pyridine/POCl₃ (Indian Journal of Heterocyclic Chemistry, 1997, 7, 25-30). 4H-1-benzopyran-4-one ring closure can then be accomplished treating the obtained 1,3-diketone in a mixture of ethanol and hydrochloric acid.

Alternatively, synthesis of compounds of formula (IV) from compounds of formula (V) where W is hydrogen (—H), alkoxy (—OR) or alkyl (—R) being R as above defined for the substituent Y, is obtained by reaction of compounds of formula (VI) where Z is a group —CO—R₅ and a compound of formula (V) as defined above, in a suitable solvent such as aqueous ethanol in the presence of sodium or potassium hydroxide (J. Med. Chem. 34, 2, 736-746, 1991; J. Med. Chem., 34, 7, 2169-76; 1991).

Synthesis of compounds of formula (IV) from compounds of formula (V), when W is hydroxy (—OH) is obtained by reaction of a compound of formula (V) with a compound of formula (VI) where Z is —CHO, being all the other substituents as defined above. For example, intermediates 2'-hydroxychalcones of formula (VII) are prepared by condensation of compounds of formula (V) (for example 5-acetamido-2-hydroxyacetophenone) and corresponding aryl or heteroaryl aldehydes of formula (V) in alkaline medium. An appropriate alkaline medium can be ethanol or methanol and 10-40% aqueous sodium hydroxide or potassium hydroxide. The condensation is carried out on stirring the reaction mixture at a temperature which can vary from 5° C. to 50° C., for a time up to 12 hours (R. B. Palkar, Indian J. Chem., 2000, 39B, 141-144). The intermediate 2-hydroxychalcone can be isolated or not. For those case isolation is necessary the cooled reaction mixture is acidified up to precipitation of the 2-hydroxychalcone. For the most of cases isolation is not necessary and the formed 2-hydroxychalcone is directly converted into the 2-aryl-3-hydroxy-1H-1-benzopyran 4-one of formula (VI) by Algar-Flynn-Oyamada reaction (Oyamada et. al., Bull. Chem. Soc. Japan, 1935, 10, 182). According to this procedure the formed chalcone is in situ oxidised adding at low temperature hydrogen peroxide (N. D. Meyer et al., J. Med. Chem., 1991, 34, 736-746).

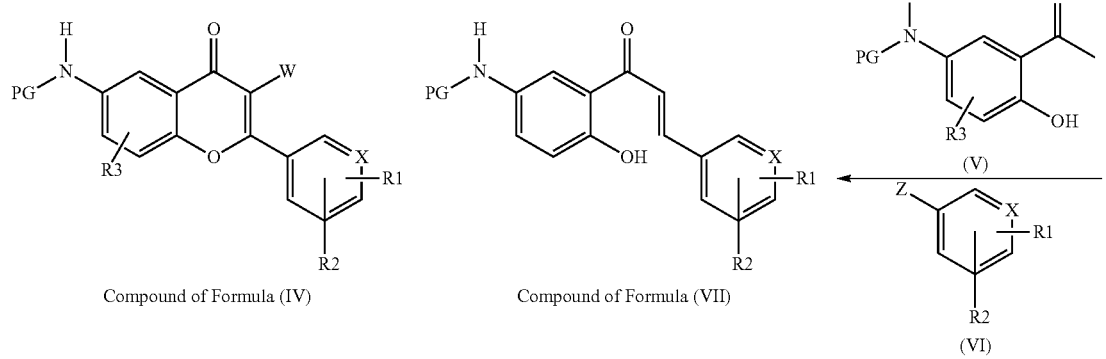

Compound of Formula (IV)   Compound of Formula (VII)   (V) (VI)

Not limiting representative examples of preparations for compounds of formula (I) are reported below.

EXAMPLE 1

2-phenyl-6-[(1-iminoethyl)amino]-4H-1-benzopyran-4-one hydrochloride

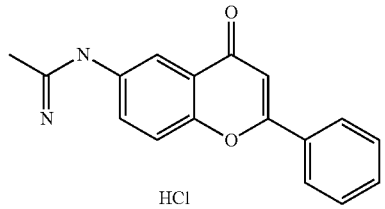 [SMILES: CC(=N)Nc1ccc2oc(-c3ccccc3)cc(=O)c2c1 ; Cl]

HCl 6-aminoflavone (10 g, 0.040 mol, commercially available, Aldrich) suspended in acetonitrile (300 mL) is cooled at 0° C., under stirring. HCl is slowly bubbled through the suspension for 3 hours. The reaction mixture is then stirred at r.t. for 3 days, then poured in isopropyl ether (450 mL) and the precipitate washed with isopropyl ether-isopropanol (1:2 v/v). The resulting solid is filtered off and crystallised from ethanol. Yield: 69%; m.p.: 278.2-278.8° C.; Elem. anal. $C_{17}H_{14}N_2O_2$*HCl; theory C, 64.87; H, 4.80; N, 8.90. found C, 64.41; H, 5.10; N, 8.64. IR (KBr): 3317, 2776, 1677, 1639, 1481, 1368 cm$^{-1}$; $^1$H-NMR (d$_6$-DMSO): 11.82 (s broad, 1H), 9.72 (s broad, 1H), 8.7 (s broad, 1H), 8.15 (m, 2H); 7.98 (m, 2H); 7.77 (dd, 1H); 7.60 (m, 3H); 7.13 (s, 1H); 2.45 (s, 3H).

EXAMPLE 2

2-(4-methoxyphenyl)-6-[(1-iminoethyl)amino]-4H-1-benzopyran-4-one hydrochloride monohydrate

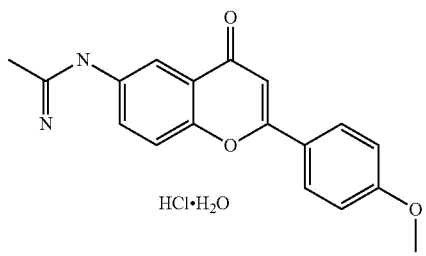

HCl•H$_2$O

Prepared analogously to Example 1, starting from 2-(4-methoxyphenyl)-6-amino-4H-1-benzopyran-4-one. Yield: 85%; m.p. 257.9-259.5° C.; Elem. anal. $C_{16}H_{16}N_2O_3$*HCl*H$_2$O; theory C, 59.59; H, 5.28; N, 7.72. found C, 59.76; H, 5.09; N, 8.52. TLC (85/25/2/1 Chloroform/Methanol/Water/Ammonia) Rf: 0.53; IR (KBr): 3381, 3211, 3060, 1648, 1605, 1511, 1257 cm$^{-1}$; $^1$H-NMR (d$_6$-DMSO): 12.0 (s broad, 1H), 9.8 (s broad, 1H), 8.7 (s broad, 1H), 8.15 (d, 2H); 7.95 (m, 2H); 7.75 (m, 1H); 7.18 (d, 2H); 7.04 (s, 1H); 3.88 (s, 3H); 2.42 (s, 3H).

2b) 2-(4-methoxyphenyl)-6-amino-4H-1-benzopyran-4-one

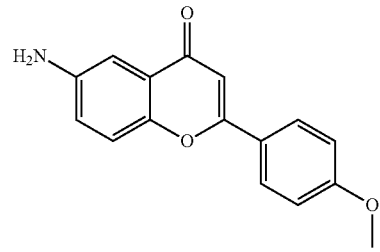 [SMILES: COc1ccc(-c2cc(=O)c3cc(N)ccc3o2)cc1]

To a suspension of 2-(4-methoxyphenyl)-6-acetamido-4H-1-benzopyran-4-one, 5 g (0.016 mol) in ethanol (solution 80% in water) (70 mL) was added H$_2$SO$_4$ 30% (25 mL) and the mixture was stirred under reflux for 4 hours. After cooling, aqueous NaOH was added until pH 10, and the mixture was extracted with dichloromethane, washed with water, dried and evaporated. Yield: 97%; TLC (85/25/2/1 Chloroform/Methanol/Water/Ammonia) Rf: 0.82.

2c) 2-(4-methoxyphenyl)-6-acetamido-4H-1-benzopyran-4-one

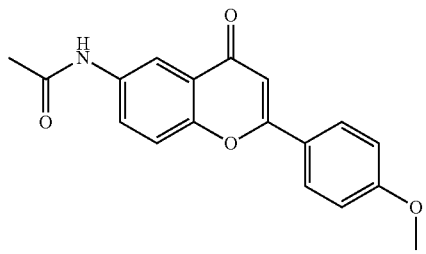

To a suspension of 2-O-(4-methoxy-benzoate)-5-acetamido-acetophenone, 18.58 g (0.0567 mol) in pyridine (120 mL) was added KOH, 6.4 g (0.113 mol) and the mixture was stirred for 8 hours at 50° C. After cooling, aqueous AcOH (20%, 300 mL) was added and the precipitate was filtered off, then suspended in glacial AcOH (130 mL) and concentrated H$_2$SO$_4$ (3 mL). The reaction mixture was stirred under reflux for 4 hours and at r.t for 16 hours. Water was added, the precipitate was filtered, washed with water, suspended in methanol, stirred for 5 minutes, filtered and dried. Yield: 71%; TLC (9/1 Chloroform/Methanol) Rf: 0.59; $^1$H-NMR (d$_6$-DMSO) 10.28 (s broad, 1H); 8.32 (d, 1H); 8.06 (d, 2H); 7.95 (dd, 1H); 7.73 (d, 1H); 7.12 (d, 2H), 6.92 (s, 1H); 2.93 (s, 3H); 2.10 (s, 3H).

2d) 2-O-(4-methoxy-benzoate)-5-acetamido-acetophenone

To a solution of 2-hydroxy-5-acetamido-acetophenone 7.0 g (0.036 mol) (J. Org. Chem., 1995, 60, 4324-4330) in pyridine (20 mL) was added 4-methoxybenzoyl chloride, 7.5 mL (0.054 mol), and the mixture was stirred for 16 hours at r.t.

Aqueous HCl was added and the mixture was extracted with DCM, washed with water, dried and concentrated. The obtained solid was suspended in methanol, stirred, filtered, washed with ethyl acetate and dried. Yield: 20%; TLC (9/1 Chloroform/Methanol) Rf: 0.52; IR (KBr): 3361, 1722, 1692, 1605, 1532, 1259, 1169 cm$^{-1}$; $^1$H-NMR (d$_6$-DMSO) 8.09 (m, 3H); 7.86 (m, 1H); 7.31-7.12 (m, 3H); 3.90 (s, 3H); 2.52 (s, 3H), 2.09 (s, 3H).

EXAMPLE 3

2-(4-fluorophenyl)-6-[(1-iminoethyl)amino]-4H-1-benzopyran-4-one

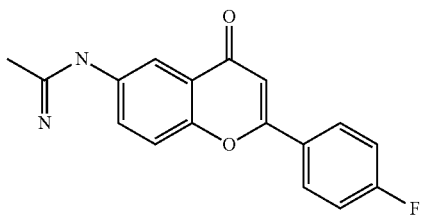 [SMILES: CC(=N)Nc1ccc2oc(-c3ccc(F)cc3)cc(=O)c2c1]

A suspension of 2-(4-fluorophenyl)-6-amino-4H-1-benzopyran-4-one, 4.5 g (0.017 mol) in acetonitrile (600 mL) was saturated with HCl gas and the mixture was stirred for 18 hours at r.t. Solvent was removed and the residue dissolved in water and washed with ethyl ether; Na$_2$CO$_3$ was added to the aqueous solution until pH 10. The aqueous phase was extracted with ethyl acetate, the organic phase was dried and concentrated. The residue was treated with boiling acetonitrile (20 mL/g), the resulting solid was filtered and dried. Yield: 61%; m.p.: 201.6-203.1° C. TLC: (85/25/2/1 Chloroform/Methanol/Water/Ammonia): Rf 0.65; IR (KBr): 3458, 3074, 1637, 1614, 1508, 1437; $^1$H-NMR (d$_6$-DMSO): 8.18 (m broad, 2H), 7.6 (m broad, 1H), 7.4 (m broad, 2H), 7.25 (m, 2H); 6.98 (s, 1H); 6.39 (m broad, 2H); 1.85 (d, 3H).

3b) 2-(4-fluorophenyl)-6-amino-4H-1-benzopyran-4-one

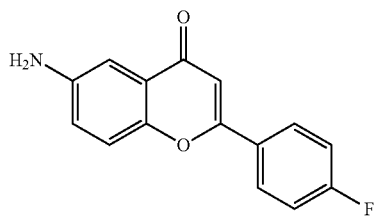 [SMILES: Nc1ccc2oc(-c3ccc(F)cc3)cc(=O)c2c1]

To a suspension of 2-O-(4-fluoro-5-benzoate)-5-acetamido-acetophenone 27.0 g (0.0856 mol) in pyridine (80 mL) was added KOH 12.0 g (0.214 mol) and the mixture was stirred for 3 hours at 50° C. and for 18 hours at r.t. HCl 2N (300 mL) was added and the resulting solid was collected and suspended in glacial AcOH (120 mL) and concentrated H$_2$SO$_4$ (5 mL). The mixture was stirred under reflux for 3 hours and then at r.t for 18 hours. Water was added, the precipitate was collected, washed with water and dried. The product was suspended in ethanol/water (80:20 v/v) (500 mL), H$_2$SO$_4$ 30% (90 mL) was added and the mixture was stirred under reflux for 24 hours. After cooling the precipitate was filtered, washed with ethanol then suspended in NaOH 1N, filtered and washed with water. The residue was dissolved in DMF (30 mL), filtered, then the solvent was removed in vacuo. The residue was suspended in ethyl acetate, stirred, filtered and dried. Yield: 30%; TLC (9/1 Chloroform/Methanol): Rf: 0.45; C, 70.03; H, 4.38; N, 5.41. $^1$H-NMR (d$_6$-DMSO): 8.13 (m, 2H), 7.43 (m, 3H); 7.12 (m, 2H), 6.88 (s, 1H); 5.54 (s broad, 2H);

3c) 2-O-(4-fluoro-5-benzoate)-5-acetamido-acetophenone

To a suspension of 2-hydroxy-5-acetamido-acetophenone (0.103 mol) in THF (500 mL) and triethylamine (0.144 mol), 4-fluoro benzoyl chloride (0.134 mol) and Dimethylaminopyridine (DMAP) (0.03 mol) were added, the reaction mixture was stirred for 2 h at r.t., then refluxed for 12 h. Solvent was evaporated, water was added and the mixture was extracted with ethyl acetate, washed with water, dried and concentrated.

EXAMPLE 4

2-(benzo[1,3]dioxol-5-yl)-6-[(1-iminoethyl)amino]-4H-1-benzopyran-4-one hydrochloride

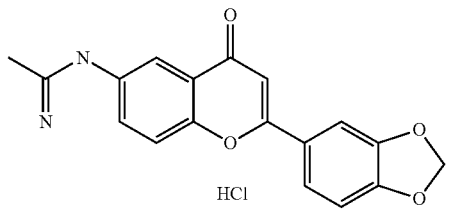 [SMILES: CC(=N)Nc1ccc2oc(-c3ccc4c(c3)OCO4)cc(=O)c2c1 ; Cl]

A suspension of 2-(benzo[1,3]dioxol-5-yl)-6-amino-4H-1-benzopyran-4-one 1.2 g (4.3 mmol) in acetonitrile (600 mL) was saturated with HCl gas and the mixture was stirred for 18 hours at r.t. Solvent was evaporated and the residue treated with methanol/ammonia then concentrated. The residue was purified by silica gel column (eluent CHCl$_3$/MeOH/NH$_3$=8/2/0.1) then suspended in methanol/HCl, stirred, filtered and dried. Yield 78%; m.p.: 272.7-273.3° C.; TLC (85/25/2/1 Chloroform/Methanol/Water/Ammonia) Rf; 0.45 Elem. anal. C$_{18}$H$_{14}$N$_2$O$_4$.HCl; theory: C, 60.25; H, 4.21; N, 7.80. found C, 58.08; H, 4.35; N, 7.79. IR (KBr): 3423, 3000, 1611, 1502, 1228; $^1$H-NMR (d$_6$-DMSO): 9.7 (s broad, 1H), 9.1 (s broad, 1H), 8.7 (s broad, 1H); 7.93 (d, 2H); 7.75 (m, 3H); 7.15 (m, 2H); 7.05 (d, 1H); 6.18 (s, 2H); 2.37 (s, 3H).

4b) 2-(benzo[1,3]dioxol-5-yl)-6-amino-4H-1-benzopyran-4-one

To a suspension of 2-O-([1,3]dioxol-5-benzoate)-5-acetamido-acetophenone 21 g (62.1 mmol) in pyridine (60 mL) was added KOH 8.7 g (0.155 mol) and the mixture was stirred for 3 hours at 50° C. and for 18 hours at r.t. HCl 2N (300 mL) was added and the precipitate was collected and re-suspended in glacial AcOH (70 mL) and concentrated H$_2$SO$_4$ (2.1 mL). The mixture was stirred under reflux for 4 hours then stirred at r.t for 16 hours. Ethyl ether was added, the precipitate was collected and washed with ethyl ether. The solid was dissolved in ethanol (solution 80% in water) (60 mL), H$_2$SO$_4$ 30% (9 mL) was added and the mixture was stirred under reflux for 18 hours. After cooling the solid was filtered, washed with ethanol then suspended in NaHCO₃ 1% in water, filtered, washed with water. Yield: 25%; TLC (9/1 Chloroform/Ethyl Acetate) Rf: 0.31, Elem. anal. C₁₆H₁₁NO₄; theory: C, 68.30; H, 3.94; N, 4.98. found C, 66.40; H, 4.06; N, 4.89.

4c) 2-O-([1,3]dioxol-5-benzoate)-5-acetamido-acetophenone

To a suspension of 2-hydroxy-5-acetamido-acetophenone, 12 g (0.062 mol), in THF (250 mL), TEA (0.081 mol), piperonyl chloride (0.054 mol) and DMAP (0.03 mol) were added, and the mixture was stirred for 24 hours at r.t. Solvent was evaporated, water was added, the precipitate was collected, washed with water and dried. Yield almost quantitative. TLC (9/1 Chloroform/Ethyl acetate) Rf: 0.80

EXAMPLE 5

2-[(4-imidazol-1-yl)-phenyl]-3-hydroxy-6-[(1-iminoethyl)amino]-4H-1-benzopyran-4-one hydrochloride

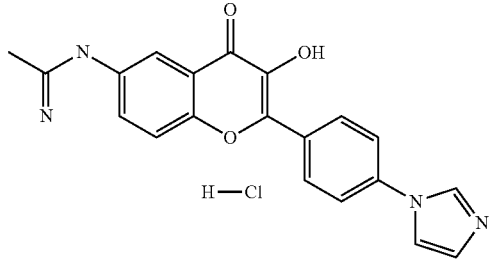

2-[(4-(imidazol-1-yl)-phenyl]-3-benzyloxy-6-[(1-iminoethyl)amino]-4H-1-benzopyran-4-one (1.6 g; 3.34 mmol) was suspended in methanol (100 mL), 3 mL of MeOH saturated with HCl were added to the reaction mixture then 10% Pd/C (160 mg.) was added. The reaction mixture was left under hydrogen bubbling for 4 hours, then the catalyst was filtered off. The solvent was removed and the remaining solid suspended in diethyl ether, then filtered. The titled compound was obtained as a yellow solid, yield: 75%; m.p.: 311.7-312.1° C.; Elem. anal.: C₂₀H₁₆N₄O₃.HCl, Theory: C, 55.44; H, 4.19; N, 12.93. Found: C, 56.09; H, 4.34; N, 13.22. TLC (8/2 Chloroform/Methanol) Rf: 0.11; IR (KBr): 2996, 2871, 1568, 1592 cm⁻¹; ¹H-NMR (d₆-DMSO): 11.89 (s, 1H); 10.27 (s, 1H); 9.81 (s, 1H) 9.71 (s, 1H); 8.81 (s, 1H); 8.50 (d, 2H); 8.4 (d, 1H); 8.01 (m, 4H); 7.93 (d, 1H); 7.77 (dd, 1H); 2.58 (d, 2H); 1.28 (m, 1H); MS (EI) 401 (M+1).

5b) 2-[(4-(imidazol-1-yl)-phenyl]-3-benzyloxy-6-[(1-iminoethyl)amino]-4H-1-benzopyran-4-one

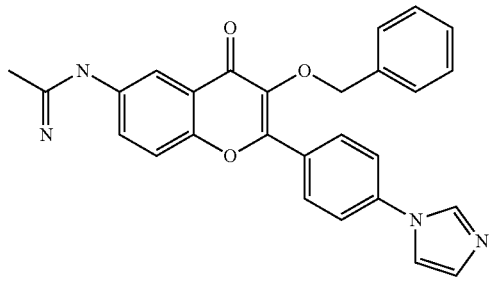 [SMILES: CC(=N)Nc1ccc2oc(-c3ccc(-n4ccnc4)cc3)c(OCc3ccccc3)c(=O)c2c1]

2-[(4-(imidazol-1-yl)-phenyl]-3-benzyloxy-6-amino-4H-1-benzopyran-4-one (3 g; 6.22 mmol) was suspended in acetonitrile (50 mL) and cooled at 0° C. HCl was bubbled into the solution upon saturation. The reaction was then stirred for 4 hours at r.t., upon completion, H₂O (20 mL) was added and the acetonitrile removed under vacuum. The solution was then brought to pH=9 with NaOH 2N, the precipitate was filtered off and dried to give the titled compound as a bright yellow solid. Yield: 73%. TLC: (9/1 Chloroform/Methanol) Rf: 0.6.

5c) 2-[(4-(imidazol-1-yl)-phenyl]-3-benzyloxy-6-amino-4H-1-benzopyran-4-one

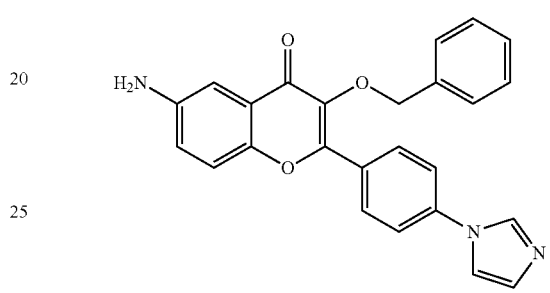

2-[(4-(imidazol-1-yl)-phenyl]-3-benzyloxy-6-acetamido-4H-1-benzopyran-4-one (7 g; 15.5 mmol) was suspended in ethanol (250 mL), HCl 4N (16 mL; 62 mmol) was added and the mixture refluxed for 24 hours. After cooling, the reaction was concentrated and the precipitate was filtered off. The crude was suspended in diisopropyl ether, filtered and dried to give the titled compound as light yellow solid. ¹H-NMR (d₆-DMSO): 9.91 (s, 1H); 8.44 (d, 1H); 8.22 (d, 2H); 7.90 (d, 3H); 7.78 (d, 2H); 7.33 (d, 1H); 7.32 (m, 6H); 5.16 (s, 2H); MS (EI) 410 (M+1), 319 (M-91).

5d) 2-[(4-(imidazol-1-yl)-phenyl]-3-benzyloxy-6-acetamido-4H-1-benzopyran-4-one

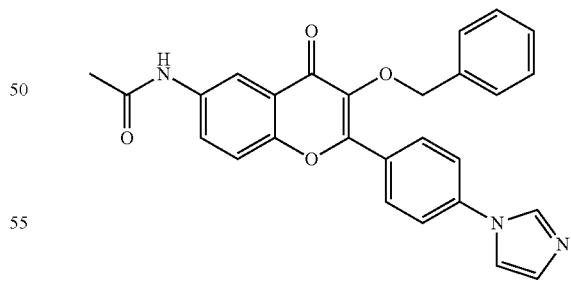

2-[(4-(imidazol-1-yl)-phenyl]-3-hydroxy-6-acetamido-4H-1-benzopyran-4-one (10 g; 25.14 mmol) was dissolved in dry acetone (300 mL). Benzyl bromide (3.6 mL; 30.16 mmol) and anhydrous K₂CO₃ (5.9 g; 42.73 mmol) were added and the mixture refluxed for 18 hours. After cooling, the reaction was quenched with H₂O and the precipitate filtered. Slurry of the latter with diisopropyl ether gave the compound as a white solid. Yield: 92%; ¹H-NMR (d₆-DMSO): 10.32 (s, 1H); 8.43

(s, 2H); 8.14 (d, 2H); 7.88 (m, 4H); 7.78 (d, 2H); 7.32 (m, 5H); 7.16 (s, 1H); 7.45 (s, 1H); 5.1 (s, 2H); 2.1 (s, 3H).

5e) 2-[(4-(imidazol-1-yl)-phenyl]-3-hydroxy-6-acetamido-4H-1-benzopyran-4-one

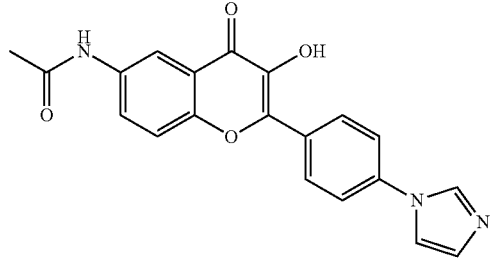 [SMILES: CC(=O)Nc1ccc2oc(-c3ccc(-n4ccnc4)cc3)c(O)c(=O)c2c1]

2-Hydroxy-4-acetamido acetophenone (6 g; 31.06 mmol) was dissolved in ethanol (100 mL), NaOH (6.2 g; 0.15 mol) and 4-imidazoyl benzaldehyde (9.6 g; 55.9 mmol) (prepared according to J. Med. Chem., 1993, 36(20), 2964-72) were then added and the resulting mixture was stirred for 24 hours at r.t. The reaction was diluted with MeOH (100 mL) then $H_2O_2$ (15 mL) followed by $H_2O$ (15 mL) were added. After 3 hours the yellow solid was filtered, suspended in HCl 3N and stirred for 1 hour at r.t. The precipitate was filtered and dried to give the titled compound as a yellow solid, yield: 77%; $^1$H-NMR ($d_6$-DMSO): 10.36 (s, 1H); 9.80 (s, 1H); 8.91 (s, 1H); 8.46 (d, 1H); 8.38 (d, 2H); 8.0 (s, 1H); 7.94 (d, 3H) 7.76 (d, 1H); 7.45 (s, 1H); 2.1 (s, 3H); MS (EI) 362 (M+1).

EXAMPLE 6

2-[(4-imidazol-1-yl)-phenyl]-3-hydroxy-6-[(1-iminoethyl-2-cyclopropyl)amino]-4H-1-benzopyran-4-one dihydrochloride monohydrate

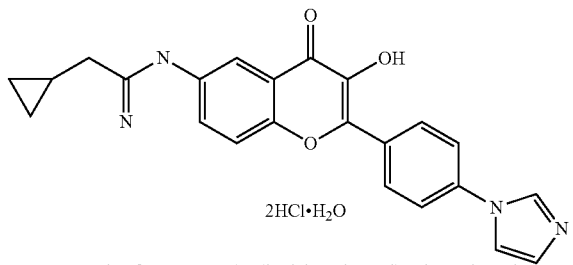 [SMILES: N=C(CC1CC1)Nc1ccc2oc(-c3ccc(-n4ccnc4)cc3)c(O)c(=O)c2c1 ; "2HCl·H2O"]

Prepared from 2-[(4-(imidazol-1-yl)-phenyl]-3-benzyloxy-6-[(1-iminoethyl-2-cyclopropyl)amino]-4H-1-benzopyran-4-one analogously to example 5. Yellow solid. Yield: 97%; m.p.: 249.1-251.1° C. Elem. anal.: $C_{23}H_{20}N_4O_3 \cdot 2HC \cdot H_2O$, Theory: C, 56.26; H, 4.29; N, 11.40. Found: C, 54.26; H, 4.53; N, 10.78. IR (KBr): 2996, 2871, 1568, 1592 cm$^{-1}$; $^1$H-NMR ($d_6$-DMSO): 8.81 (s, 1H); 8.50 (d, 2H); 8.4 (d, 1H); 8.01 (m, 4H); 7.93 (d, 1H); 7.77 (dd, 1H); 2.58 (d, 2H); 1.28 (m, 1H); 0.6 (m, 1H); 0.4 (m, 1H); MS (EI) 401 (M+1).

6b) 2-[(4-(imidazol-1-yl)-phenyl]-3-benzyloxy-6-[(1-iminoethyl-2-cyclopropyl)amino]-4H-1-benzopyran-4-one

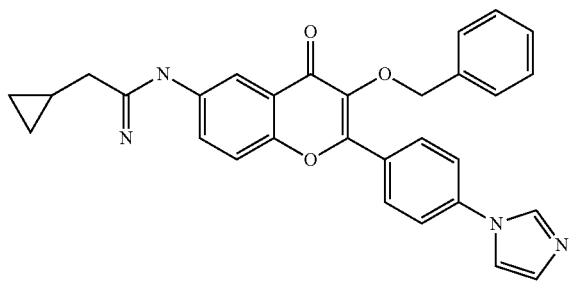 [SMILES: N=C(CC1CC1)Nc1ccc2oc(-c3ccc(-n4ccnc4)cc3)c(OCc3ccccc3)c(=O)c2c1]

Prepared analogously to example 5b) except that cyclopropyl acetonitrile was used instead of acetonitrile. Yellow solid. Yield 79%. TLC: (9/1 Chloroform/Methanol) Rf: 0.48.

EXAMPLE 7

2-[(4-(imidazol-1-yl)-phenyl]-3-hydroxy-6-[(1-iminopropyl-3-methoxy)amino]-4H-1-benzopyran-4-one

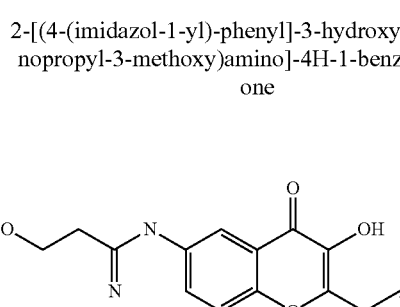

Prepared analogously to example 5. Yellow solid. Yield: 76%. $^1$H-NMR ($d_4$-CD$_3$OD): 8.64 (s, 1H); 7.81 (d, 2H); 7.35 (d, 2H); 7.16 (d, 4H); 6.98 (d, 1H); 6.93 (d, 1H); 3.07 (t, 2H); 2.68 (s, 3H); 2.17 (t, 2H). MS (EI) 405 (M+1).

2-[(4-(imidazol-1-yl)-phenyl]-3-benzyloxy-6-[(1-iminopropyl-3-methoxy)amino]-4H-1-benzopyran-4-one

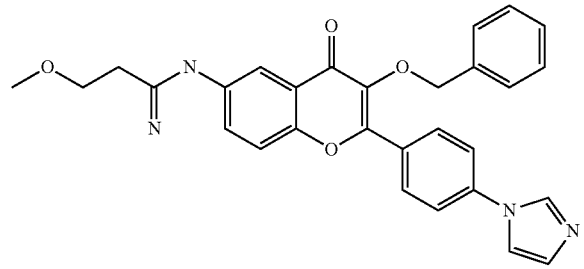 [SMILES: COCCC(=N)Nc1ccc2oc(-c3ccc(-n4ccnc4)cc3)c(OCc3ccccc3)c(=O)c2c1]

Prepared analogously to example 5b) except that 3-methoxypropionitrile was used instead of acetonitrile. Yellow solid. Yield 50%. TLC (9/1 Chloroform/Methanol) Rf: 0.18.

EXAMPLE 8

2-[(3-(imidazol-1-yl)-phenyl]-3-hydroxy-6-[(1-iminoethyl)amino]-4H-1-benzopyran-4-one dihydrochloride

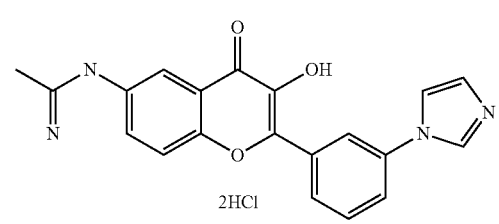 [SMILES: CC(=N)Nc1ccc2oc(-c3cccc(-n4ccnc4)c3)c(O)c(=O)c2c1]

Prepared analogously to Example 5, starting from 2-[(3-(imidazol-1-yl)-phenyl]-3-benzyloxy-6-[(1-iminoethyl)amino]-4H-1-benzopyran-4-one dihydrochloride. Yield: 90%; m.p.: 281.0-281.5° C. TLC (80/20/2 Chloroform/Methanol/Ammonia) Rf: 0.32; Elem. anal.: $C_{20}H_{16}N_4O_3 \cdot 2HCl$, Theory: C, 55.44; H, 4.19; N, 12.93. Found: C, 53.05; H, 4.34; N, 12.18. $^1$H-NMR ($d_6$-DMSO): 11.83 (s broad, 1H), 10.30 (s, 1H), 9.75 (m, 2H), 8.73 (s broad, 1H), 8.46 (m, 2H), 8.38 (m, 1H), 8.07-7.75 (m, 6H), 2.41 (s, 3H).

2-[(3-(imidazol-1-yl)-phenyl]-3-benzyloxy-6-[(1-iminoethyl)amino]-4H-1-benzopyran-4-one dihydrochloride Prepared analogously to Example 5b starting from 2-[(3-(imidazol-1-yl)-phenyl]-3-benzyloxy-6-amino-4H-1-benzopyran-4-one dihydrochloride. Yield: 55%; Rf (80/10/1 Chloroform/Methanol/Ammonia): 0.27; $^1$H-NMR ($d_6$-DMSO): 11.70 (s broad, 1H), 9.69 (s broad, 1H), 9.51 (s, 1H), 8.75 (s broad, 1H), 8.32 (m, 1H), 8.17-8.08 (m, 3H), 8.01-7.96 (m, 2H), 7.85-7.75 (m, 3H), 7.46 (s broad, 1H), 7.32-7.21 (m, 5H), 6.96 (s broad, 1H), 5.20 (s, 2H), 2.41 (s, 3H).

2-[(3-(imidazol-1-yl)-phenyl]-3-benzyloxy-6-amino-4H-1-benzopyran-4-one dihydrochloride Prepared analogously Example 5c, starting from 2-[(3-(imidazol-1-yl)-phenyl]-3-benzyloxy-6-acetamido-4H-1-benzopyran-4-one Yield: 74%; TLC (90/10/1 Chloroform/Methanol/Ammonia) Rf: 0.55; $^1$H-NMR ($d_6$-DMSO): 9.66 (s, 1H), 8.28 (m, 1H), 8.21 (m, 1H), 8.13 (dd, 1H), 7.95 (m, 2H), 7.78 (m, 1H), 7.60 (m, 1H), 7.42 (d, 1H), 7.35-7.2 (m, 6H), 5.16 (s, 2H).

2-[(3-(imidazol-1-yl)-phenyl]-3-benzyloxy-6-acetamido-4H-1-benzopyran-4-one

Prepared analogously to Example 5.d, starting from 2-[(3-(imidazol-1-yl)-phenyl]-3-hydroxy-6-acetamido-4H-1-benzopyran-4-one. Yield: 55%; TLC (85/15 Chloroform/Methanol) Rf: 0.64; $^1$H-NMR ($d_6$-DMSO): 10.28 (s broad, 1H), 8.44 (d, 1H), 8.23-8.16 (m, 2H), 8.04-7.9 (m, 2H), 7.85-7.65 (m, 4H), 7.27 (m, 4H), 7.14 (m, 1H), 5.17 (s, 2H), 2.12 (s, 3H).

2-[(3-(imidazol-1-yl)-phenyl]-3-hydroxy-6-acetamido-4H-1-benzopyran-4-one

Prepared analogously to Example 5.e, except that aqueous $NaHCO_3$ was added to the obtained hydrochloride and the mixture was extracted with ethyl acetate, washed with water, dried, evaporated and triturated in methanol. Yield: 10%; $^1$H-NMR ($d_6$-DMSO): 10.29 (s broad, 1H), 9.84 (s broad, 1H), 8.45 (d, 1H), 8.35 (m, 2H), 8.24 (dd, 1H), 7.95-7.68 (m, 5H), 7.17 (m, 1H), 2.07 (s, 3H).

EXAMPLE 9

2-(4-methansulfonylphenyl)-3-hydroxy-6-[(1-iminoethyl)amino]-4H-1-benzopyran-4-one hydrochloride

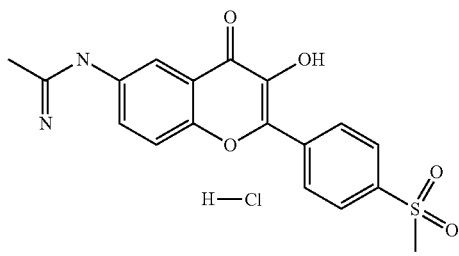

2-(4-methansulfonylphenyl)-3-benzyloxy-6-[(1-iminoethyl)amino]-4H-1-benzopyran-4-one (0.19 g; 0.41 mmol) was suspended in acetonitrile (40 mL) and cooled at 0° C. HCl was bubbled into the solution upon saturation. The reaction was then stirred for 24 hours at r.t. Upon completion, $H_2O$ (20 mL) was added and the acetonitrile removed under vacuum. The solution was then brought to pH=9 with NaOH 2N. The solution was concentrated and the precipitate filtered off and dried to afford the titled compound as yellow solid. Yield: 35%. TLC (85/25/1/2 Chloroform/Methanol/Ammonia/Water) Rf: 0.15. Elem. anal.: $C_{18}H_{16}N_2O_5S \cdot HCl$, Theory: C, 52.88; H, 4.19; N, 6.85. Found: C, 51.09; H, 4.08; N, 5.81. $^1$H-NMR ($d_4$-$CD_3OD$): 8.57 (d, 2H); 8.12 (dd, 3H); 7.90 (d, 1H); 7.72 (dd, 1H); 3.18 (s, 3H); 2.17 (s, 3H).

2-(4-methansulfonylphenyl)-3-benzyloxy-6-amino-4H-1-benzopyran-4-one

Prepared analogously to example 5c). Yield: 99%. $^1$H-NMR ($d_6$-DMSO): 8.15 (d, 2H); 8.04 (d, 2H); 7.34-7.25 (m, 7H); 5.12 (s, 2H); 3.3 (s, 3H). TLC (9/1 Chloroform/Methanol) Rf: 0.7.

2-(4-methansulfonylphenyl)-3-benzyloxy-6-acetamido-4H-1-benzopyran-4-one

Prepared analogously to example 5d). Light yellow oil. Yield: 23%. TLC (9/1 Chloroform/Ethyl Acetate) Rf: 0.25.

2-(4-methansulfonylphenyl)-3-hydroxy-6-acetamido-4H-1-benzopyran-4-one

Prepared analogously to example 5e). White solid. Yield: 20%. $^1$H-NMR ($d_6$-DMSO): 10.29 (s, 1H); 10.08 (s, 1H); 8.45 (dd, 3H); 8.11 (d, 2H); 7.94 (d, 1H); 7.76 (d, 1H); 3.29 (s, 3H); 2.1 (s, 3H). TLC (9/1 Chloroform/Methanol) Rf: 0.65.

EXAMPLE 10

2-(3,4-dihydroxyphenyl)-3-hydroxy-6-[(1-iminoethyl)amino]-4H-1-benzopyran-4-one hydrochloride

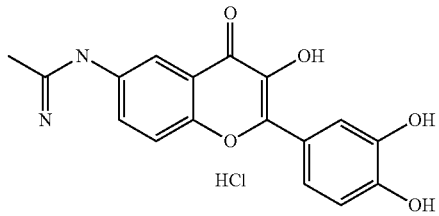 [SMILES: CC(=N)Nc1ccc2oc(-c3ccc(O)c(O)c3)c(O)c(=O)c2c1 ; Cl]

Prepared analogously to example 5, but the titled compound was purified by suspension in diisopropyl ether. Yellow solid. Yield: 25%; m.p: 310.1-310.9° C. $^1$H-NMR (d$_6$-DMSO): 11.53 (br s, 1H); 9.72 (s, 1H); 9.55 (s, 1H); 9.36 (s, 1H); 8.64 (s, 1H); 8.01 (d, 1H); 7.90 (d, 2H); 7.78 (d, 1H); 7.35 (d, 2H); 7.65 (dt, 2H); 6.93 (d, 1H); 3.35 (s, 3H).

b) 2-(3,4-dibenzyloxyphenyl)-3-hydroxy-6-[(1-iminoethyl)amino]-4H-1-benzopyran-4-one 2-(3,4-dibenzyloxyphenyl)-3-hydroxy-6-amino-4H-1-benzopyran-4-one (1.9 g; 3.78 mmol) was suspended in acetonitrile (40 mL) and cooled at 0° C. HCl was bubbled into the solution upon saturation. The reaction was then stirred for 5 days at r.t. Upon completion, H$_2$O (20 mL) was added and the acetonitrile removed under vacuum. The precipitate was filtered off and dried to afford the titled compound as a bright yellow solid. Yield: 92%. TLC (9/1 Chloroform/Methanol) Rf: 0.2. $^1$H-NMR (d$_6$-DMSO): 11.61 (br s, 1H); 9.62 (s, 1H); 8.65 (s, 1H); 8.01 (d, 1H), 7.90 (d, 2H); 7.78 (d, 1H); 7.35 (d, 2H); 7.65 (dt, 2H); 6.93 (d, 1H); 3.35 (s, 3H)

c) 2-(3,4-dibenzyloxyphenyl)-3-hydroxy-6-amino-4H-1-benzopyran-4-one

Prepared analogously to example 5c). Light green solid. Yield: 84%. $^1$H-NMR (d$_6$-DMSO): 9.61 (s, 1H); 7.91-7.83 (m, 2H); 7.69-7.24 (m, 16H); 5.26 (s, 2H); 5.22 (s, 2H). MS (EI) 466 (M+1).

d) N2-(3,4-dibenzyloxyphenyl)-3-hydroxy-6-amino-4H-1-benzopyran-4-one

Prepared analogously to example 5d) but using 3,4-dibenzyloxy benzaldehyde. Light green solid. Yield: 2.5 g (10%). $^1$H-NMR (d$_6$-DMSO): 10.26 (br s, 1H); 9.46 (br s, 1H); 8.41 (d, 1H); 7.92-7.84 (m, 4H); 7.74-7.24 (m, 15H); 5.25 (s, 2H), 5.22 (s, 2H); 2.1 (s, 3H).

EXAMPLE 11

2-(4-hydroxyphenyl-3-hydroxy-6-[(1-iminoethyl-2-cyclopropyl)amino]-4H-1-benzopyran-4-one hydrochloride

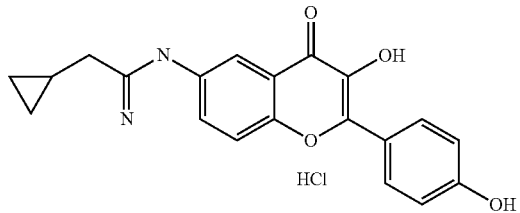 [SMILES: N=C(CC1CC1)Nc1ccc2oc(-c3ccc(O)cc3)c(O)c(=O)c2c1 ; Cl]

Prepared analogously to Example 5, starting from 2-(4-hydroxyphenyl-3-benzyloxy-6-[(1-iminoethyl-2-cyclopropyl)amino]-4H-1-benzopyran-4-one hydrochloride. Yield: 90%; m.p. 281.0-281.5° C. TLC (85/25/2/1 Chloroform/Methanol/Water/Ammonia) Rf: 0.47; Elem. anal.: C$_{20}$H$_{18}$N$_2$O$_4$.HCl, Theory: C, 62.10; H, 4.95; N, 7.24. Found: C, 58.35; H, 5.12; N, 6.85. IR (KBr): 3327, 3114, 3066, 1676, 1599, 1553, 1486, 1274 cm$^{-1}$; $^1$H-NMR (d$_6$-DMSO): 10.25 (s broad, 1H), 9.58 (s broad, 2H), 8.15 (d, 2H), 8.1-7.9 (m, 2H), 7.7 (dd, 1H); 6.98 (d, 2H); 1.26 (m, 1H), 0.7-0.4 (m, 4H).

b) 2-(4-hydroxyphenyl-3-benzyloxy-6-[(1-iminoethyl-2-cyclopropyl)amino]-4H-1-benzopyran-4-one hydrochloride Prepared analogously to Example 5b, starting from 2-(4-hydroxyphenyl)-3-benzyloxy-6-amino-4H-1-benzopyran-4-one hydrochloride, but the product was purified by suspension in methanol. Yield: 50%; TLC (9/1 Chloroform/Methanol) Rf: 0.30.

c) 2-(4-hydroxyphenyl)-3-benzyloxy-6-amino-4H-1-benzopyran-4-one hydrochloride

Prepared analogously to Example 5c, starting from 2-(4-hydroxyphenyl)-3-benzyloxy-6-acetamido-4H-1-benzopyran-4-one. Yield: 82%; TLC (9/1 Chloroform/Methanol) Rf: 0.71 Elem. anal. C$_{29}$H$_{23}$NO$_4$*HCl; theory C, 71.68; H, 4.98; N, 2.88. found C, 71.35; H, 4.76; N, 3.03. $^1$H-NMR (d$_6$-DMSO): 8.02 (d, 2H), 7.8-7.7 (m, 2H), 7.55-7.25 (m, 11H), 7.18 (d, 2H), 5.22 (s, 2H), 5.08 (s, 2H).

d) 2-(4-hydroxyphenyl)-3-benzyloxy-6-acetamido-4H-1-benzopyran-4-one

Prepared analogously to Example 5d, starting from 2-(4-hydroxyphenyl)-3-hydroxy-6-acetamido-4H-1-benzopyran-4-one. Yield: 84%; Rf (9/1 Chloroform/Methanol): 0.59, $^1$H-NMR (d$_6$-DMSO): 10.38 (s broad, 1H), 8.40 (d, 1H), 8.1-7.9 (m, 3H), 7.70 (d, 1H); 7.55-7.25 (m, 10H); 7.17 (d, 2H); 5.22 (s, 2H), 5.07 (s, 2H); 2.11 (s, 3H).

EXAMPLE 12

2-(4-methoxyphenyl)-3-hydroxy-6-[(1-iminoethyl)amino]-4H-1-benzopyran-4-one hydrochloride monohydrate

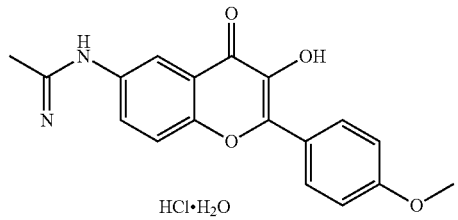 [SMILES: COc1ccc(-c2oc3ccc(NC(C)=N)cc3c(=O)c2O)cc1 ; "HCl·H2O"]

Prepared analogously to Example 5 starting from 2-(4-methoxyphenyl)-3-benzyloxy-6-[(1-iminoethyl)amino]-4H-1-benzopyran-4-one. Yield: 90%; m.p.: 260.1-261.1° C. Rf (85/25/2/1 Chloroform/Methanol/Water/Ammonia): 0.39; Elem. anal. C$_{18}$H$_{16}$N$_2$O$_4$*HCl*H$_2$O; theory C, 57.07; H, 5.06; N, 7.39. found C, 55.80; H, 4.62; N, 7.70. $^1$H-NMR (d$_6$-DMSO): 11.7 (s broad, 1H), 9.68 (m, 2H), 8.57 (s broad, 1H), 8.23 (d, 2H), 7.98 (m, 2H); 7.72 (dd, 1H); 7.15 (d, 2H); 3.86 (s, 3H); 2.50 (s, 3H).

b) 2-(4-methoxyphenyl)-3-benzyloxy-6-[(1-iminoethyl)amino]-4H-1-benzopyran-4-one Prepared analogously to Example 5b) starting from 2-(4-methoxyphenyl)-3-benzyloxy-6-amino-4H-1-benzopyran-4-one hydrochloride. Yield: 80%.

c) 2-(4-methoxyphenyl)-3-benzyloxy-6-amino-4H-1-benzopyran-4-one hydrochloride Prepared analogously to Example 5c) starting from 2-(4-methoxyphenyl)-3-benzyloxy-6-acetamido-4H-1-benzopyran-4-one. Yield: 54%; TLC (9/1 Chloroform/Methanol) Rf: 0.60; Elem. anal. $C_{23}H_{19}NO_4 \cdot HCl$; theory C, 67.40; H, 4.92; N, 3.42. found C, 64.24; H, 4.73; N, 3.20. IR (KBr): 3433, 2833, 2592, 1629, 1498, 1167 cm$^{-1}$, $^1$H-NMR (d$_6$-DMSO): 8.0 (m, 2H), 7.73 (m, 2H), 7.52 (dd, 1H), 7.37-7.22 (m, 5H), 7.10 (m, 2H).

d) 2-(4-methoxyphenyl)-3-benzyloxy-6-acetamido-4H-1-benzopyran-4-one

Prepared analogously to Example 5d) starting from 2-(4-methoxyphenyl)-3-hydroxy-6-acetamido-4H-1-benzopyran-4-one. Yield: 95%; TLC (9/1 Chloroform/Methanol) Rf: 0.51; $^1$H-NMR (d$_6$-DMSO): 10.31 (s broad, 1H), 8.40 (d, 1H), 8.02 (m, 3H), 7.70 (d, 1H), 7.32 (m, 5H), 7.11 (d, 2H), 5.08 (s, 2H), 3.86 (s, H), 2.11 (s, 3H).

e) 2-(4-methoxyphenyl)-3-hydroxy-6-acetamido-4H-1-benzopyran-4-one

Prepared analogously to Example 5e. Yield: 80%.

EXAMPLE 13

2-(4-methoxyphenyl)-3-hydroxy-6-[(1-iminoethyl-2-hydroxy)amino]-4H-1-benzopyran-4-one hydrochloride monohydrate

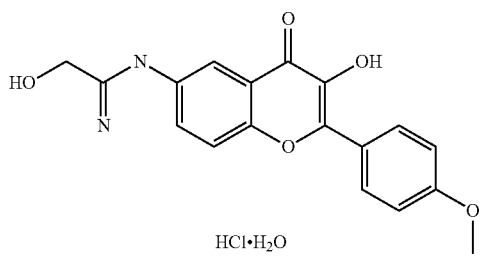 [SMILES: COc1ccc(-c2oc3ccc(NC(=N)CO)cc3c(=O)c2O)cc1 ; "HCl·H2O"]

Prepared analogously to Example 5, starting from 2-(4-methoxyphenyl)-3-benzyloxy-6-[(1-iminoethyl-2-hydroxy)amino]-4H-1-benzopyran-4-one. Yield: 37%; TLC (85/25/2/1 Chloroform/Methanol/Water/Ammonia) Rf: 0.33; Elem. anal. $C_{19}H_{18}N_2O_5 \cdot HCl \cdot H_2O$; theory C, 55.82; H, 5.18; N, 6.85. found C, 53.22; H, 4.73; N, 6.85. $^1$H-NMR (d$_6$-DMSO): 11.6 (s broad, 1H), 9.7 (s broad, 1H), 8.8 (s broad, 1H), 8.25 (d, 2H), 8.0 (m, 2H); 7.70 (dd, 1H); 7.16 (d, 2H), 3.87 (s, 3H); 2.77 (m, 2H).

b) 2-(4-methoxyphenyl)-3-benzyloxy-6-[(1-iminoethyl-2-hydroxy)amino]-4H-1-benzopyran-4-one A suspension of 2-(4-methoxyphenyl)-3-benzyloxy-6-amino-4H-1-benzopyran-4-one hydrochloride (0.036 mol) in hydroxyacetonitrile (20 mL) was saturated with HCl gas and the mixture was stirred for 3 days at r.t. Isopropyl ether-ethyl acetate was added and the solid was filtered off. Yield: 15%.

EXAMPLE 14

N-[2-(4-methoxyphenyl)-3-hydroxy-4H-1-benzopyran-4-one-6-yl]-4-methoxybenzene carboxiimidamide hydrochloride

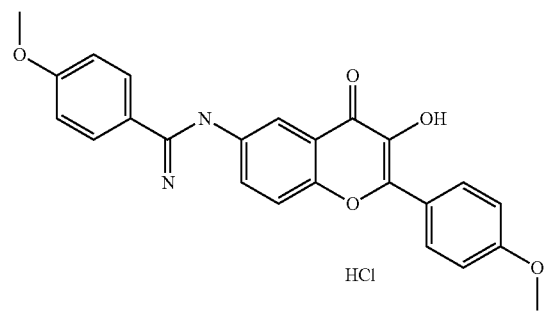 [SMILES: COc1ccc(C(=N)Nc2ccc3oc(-c4ccc(OC)cc4)c(O)c(=O)c3c2)cc1 ; Cl]

Prepared analogously to Example 5, starting from N-[2-(4-methoxyphenyl)-3-benzyloxy-4H-1-benzopyran-4-one-6-yl]-4-methoxybenzene carboxiimidamide hydrochloride. Yield: 77%; TLC (85/25/2/1 Chloroform/Methanol/Water/Ammonia) Rf: 0.71; Elem. anal. $C_{24}H_{20}N_2O_5 \cdot HCl$; theory C, 58.91; H, 4.53; N, 6.72. found C, 58.49; H, 5.62; N, 7.24. IR (KBr): 3388, 3166, 1646, 1605, 1251, 1180 cm$^{-1}$; $^1$H-NMR (d$_6$-DMSO): 11.39 (s broad, 1H), 9.72 (s broad, 1H), 9.0 (s broad, 1H), 8.2 (m, 1H), 8.0-7.8 (m, 5H); 7.2-6.9 (m, 5H); 3.92-3.81 (m, 6H).

b) 2-(4-methoxyphenyl)-3-benzyloxy-6-[(1-iminoethyl-2-hydroxy)amino]-4H-1-benzopyran-4-one hydrochloride A suspension of 2-(4-methoxyphenyl)-3-benzyloxy-6-amino-4H-1-benzopyran-4-one hydrochloride (2.44 mmol) and 4-methoxy-benzonitrile (24.4 mmol) in dioxane (100 ml) was saturated with HCl gas and the mixture was stirred for 16 hours at r.t. The solvent was evaporated and the resulting solid was used directly in the next step.

EXAMPLE 15

2-(dihydrobenzofuran-5-yl)-3-hydroxy-6-[(1-iminoethyl)amino]-4H-1-benzopyran-4-one hydrochloride

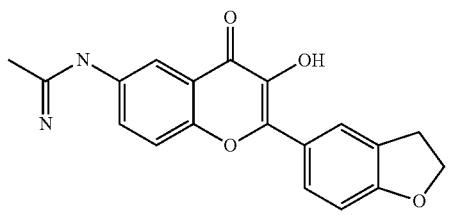 [SMILES: CC(=N)Nc1ccc2oc(-c3ccc4c(c3)CCO4)c(O)c(=O)c2c1]

Prepared analogously to Example 5b starting from 2-(dihydrobenzofuran-5-yl)-3-hydroxy-6-amino-4H-1-benzopyran-4-one hydrochloride. Yield: 54%; m.p. 291.0-292.0° C.;

TLC (85/25/2/1 Chloroform/Methanol/Water/Ammonia) Rf: 0.34; Elem. anal.: $C_{19}H_{16}N_2O_4 \cdot HCl$, Theory: C, 61.21; H, 4.60; N, 7.51. Found: C, 59.33; H, 4.61; N, 6.99. $^1H$-NMR ($d_6$-DMSO): 11.75 (s broad, 1H), 9.68 (s broad, 2H), 8.6 (s broad, 1H), 8.17-7.90 (m, 4H); 7.70 (dd, 1H); 4.65 (t, 2H); 3.31 (t, 2H); 2.40 (s, 3H). MS (EI) 337 (M+1).

b) 2-(dihydrobenzofuran-5-yl)-3-hydroxy-6-amino-4H-1-benzopyran-4-one hydrochloride Prepared analogously to Example 5c) starting from 2-(dihydrobenzofuran-5-yl)-3-hydroxy-6-acetamido-4H-1-benzopyran-4-one. Yield: 59%; TLC (9/1 Ethyl acetate/Methanol) Rf: 0.72; IR (KBr): 3444, 3232, 1607, 1546, 1492, 1297 cm$^{-1}$; $^1H$-NMR ($d_6$-DMSO): 9.13 (s broad, 1H), 8.10-7.97 (m, 2H), 7.50 (d, 1H), 7.25 (d, 1H), 7.15 (dd, 5H); 6.95 (d, 1H); 4.63 (t, 2H), 3.27 (t, 2H).

c) 2-(dihydrobenzofuran-5-yl)-3-hydroxy-6-acetamido-4H-1-benzopyran-4-one

Prepared analogously to Example 5d). Yield: 72%; TLC (9/1 Ethyl acetate/Methanol) Rf: 0.68; IR (KBr): 3371, 1671, 1577, 1493 cm$^{-1}$; $^1H$-NMR ($d_6$-DMSO): 10.24 (s broad, 1H), 9.3 (s broad, 1H), 8.40 (d, 1H), 8.11-7.8 (m, 3H), 7.7 (d, 1H), 6.94 (d, 1H); 4.63 (t, 2H); 3.30 (m, 2H), 2.1 (s, 3H).

EXAMPLE 16

2-(benzo[1,3]dioxol-5-yl)-3-hydroxy-6-[(1-iminoethyl)amino]-4H-1-benzopyran-4-one hydrochloride

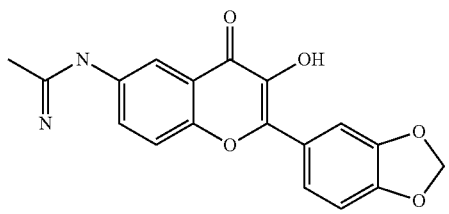 [SMILES: CC(=N)Nc1ccc2oc(-c3ccc4c(c3)OCO4)c(O)c(=O)c2c1]

Prepared analogously to Example 5b) starting from 2-(benzo[1,3]dioxol-5-yl)-3-hydroxy-6-amino-4H-1-benzopyran-4-one. Yield: 27%; m.p.: 262.3-262.9° C. TLC (5/2/2 Butanol/Acetic acid/water) Rf: 0.45. Elem. anal.: $C_{18}H_{14}N_2O_5 \cdot HCl$, Theory: C, 57.68; H, 4.03; N, 7.47. Found: C, 58.32; H, 4.53, N: 7.17. $^1H$-NMR ($d_6$-DMSO): 11.65 (s broad, 1H), 9.82-9.64 (m, 2H), 8.66 (s broad, 1H), 8.02-7.73 (m, 5H); 7.16 (m, 2H); 6.16 (s, 2H); 2.5 (s, 3H).

b) 2-(benzo[1,3]dioxol-5-yl)-3-hydroxy-6-amino-4H-1-benzopyran-4-one

Prepared analogously to Example 5c) starting from 2-(benzo[1,3]dioxol-5-yl)-3-hydroxy-6-acetamido-4H-1-benzopyran-4-one, purification of the titled product was achieved by suspending the crude in aqueous ammonia, washing with water and drying. Yield: 76%; TLC (5/2/2 Butanol/Acetic acid/water) Rf: 0.81; $^1H$-NMR ($d_6$-DMSO): 9.21 (s broad, 1H), 7.76 (m, 2H), 7.48 (m, 1H), 7.13-6.90 (m, 3H), 6.14 (s, 2H); 5.46 (s, 2H).

c) 2-(benzo[1,3]dioxol-5-yl)-3-hydroxy-6-acetamido-4H-1-benzopyran-4-one

Prepared analogously to Example 5d). Yield: 60%; TLC (9/1 Chloroform/Methanol) Rf: 0.15.

EXAMPLE 17

2-(benzo[1,3]dioxol-5-yl)-3-hydroxy-6-[(1-iminoethyl-2-cyclopropyl)amino]-4H-1-benzopyran-4-one hydrochloride

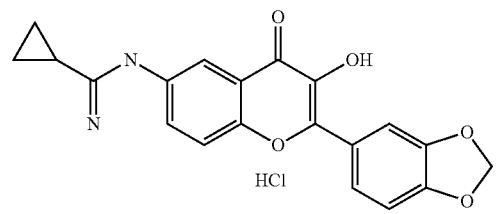

Prepared analogously to Example 5 starting from 2-(benzo[1,3]dioxol-5-yl)-3-benzyloxy-6-[(1-iminoethyl-2-cyclopropyl)amino]-4H-1-benzopyran-4-one hydrochloride. Yield: 20%; TLC (85/25/2/1 Chloroform/Methanol/Water/Ammonia) Rf: 0.49; Elem. anal.: $C_{20}H_{16}N_2O_5 \cdot HCl$, Theory: C, 60.80; H, 4.62; N, 6.75. Found: C, 60.34; H, 4.30; N, 6.44. $^1H$-NMR ($d_6$-DMSO): 11.7 (s broad, 1H), 9.8-9.6 (m, 2H), 8.7 (s broad, 1H), 8.0-7.96 (m, 2H), 7.9 (dd, 1H); 7.81 (d, 1H); 7.78 (dd, 1H), 7.16 (d, 1H), 6.16 (s, 2H), 2.57 (m, 2H), 1.26 (m, 1H), 0.60 (m, 2H), 0.44 (m, 2H).

b) 2-(benzo[1,3]dioxol-5-yl)-3-benzyloxy-6-[(1-iminoethyl-2-cyclopropyl)amino]-4H-1-benzopyran-4-one hydrochloride Prepared analogously to Example 5b) starting from 2-(benzo[1,3]dioxol-5-yl)-3-benzyloxy-6-amino-4H-1-benzopyran-4-one hydrochloride. Yield: 10%. TLC (85/25/2/1 Chloroform/Methanol/Water/Ammonia) Rf: 0.64.

c) 2-(benzo[1,3]dioxol-5-yl)-3-benzyloxy-6-amino-4H-1-benzopyran-4-one hydrochloride Prepared analogously to Example 5c) starting from 2-(benzo[1,3]dioxol-5-yl)-3-benzyloxy-6-acetamido-4H-1-benzopyran-4-one, but the purification was carried out by suspending the crude in aqueous ammonia, filtering and washing with water and then with methanol. Yield: 60%; TLC (9/1 Chloroform/Methanol) Rf: 0.51; $^1H$-NMR ($d_6$-DMSO):

7.57 (dd, 1H), 7.50-7.43 (m, 2H), 7.37-7.28 (m, 5H), 7.16-7.04 (m, 3H), 6.13 (s, 2H); 5.53 (s broad, 2H), 5.05 (s, 2H).

d) 2-(benzo[1,3]dioxol-5-yl)-3-benzyloxy-6-acetamido-4H-1-benzopyran-4-one

Prepared analogously to Example 5d) starting from 2-(benzo[1,3]dioxol-5-yl)-3-hydroxy-6-acetamido-4H-1-benzopyran-4-one. Yield: 85%; TLC (9/1 Chloroform/Methanol) Rf: 0.57.

EXAMPLE 18

2-(benzo[1,3]dioxol-5-yl)-3-hydroxy-6-[1-iminoethyl-2-cyclopropylmethyl)amino]-4H-1-benzopyran-4-one

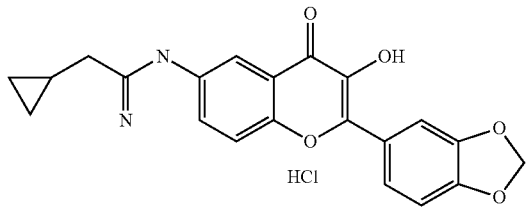 [SMILES: N=C(CC1CC1)Nc1ccc2oc(-c3ccc4c(c3)OCO4)c(O)c(=O)c2c1 ; Cl]

Prepared analogously to Example 5, starting from 2-(benzo[1,3]dioxol-5-yl)-3-benzyloxy-6-[(1-iminoethyl-2-cyclopropylmethyl)amino]-4H-1-benzopyran-4-one, except that the reaction is carried out without HCl. Yield: 25%; TLC (85/25/2/1 Chloroform/Methanol/Water/Ammonia) Rf: 0.33; Elem. anal.: $C_{21}H_{18}N_2O_5 \cdot HCl$, Theory: C, 65.93; H, 4.43; N, 7.69. Found: C, 65.36; H, 4.27; N, 6.83. $^1$H-NMR ($d_6$-DMSO): 7.85-7.75 (m, 2H), 7.66 (d, 1H), 7.39 (d, 1H), 7.19 (dd, 1H), 7.1 (d, 1H); 6.14 (d, 2H); 1.62 (m, 1H), 1.98 (m, 2H), 0.81 (m, 2H).

b) 2-(benzo[1,3]dioxol-5-yl)-3-benzyloxy-6-[(1-iminoethyl-2-cyclopropylmethyl)amino]-4H-1-benzopyran-4-one Prepared analogously to Example 5.b) starting from 2-(benzo[1,3]dioxol-5-yl)-3-benzyloxy-6-amino-4H-1-benzopyran-4-one, but the obtained hydrochloride was treated with aqueous NaOH, the product was extracted with ethyl acetate, the organic layer washed with water, dried, and evaporated to provide the titled product. Yield: 15% TLC (85/25/2/1 Chloroform/Methanol/Water/Ammonia) Rf: 0.55.

EXAMPLE 19

2-(benzo[1,3]dioxol-5-yl)-3-hydroxy-6-[(1-iminopropyl-3-methoxy)amino]-4H-1-benzopyran-4-one hydrochloride

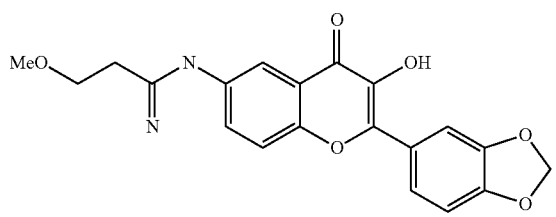 [SMILES: COCCC(=N)Nc1ccc2oc(-c3ccc4c(c3)OCO4)c(O)c(=O)c2c1]

Prepared analogously to Example 5, starting from 2-(benzo[1,3]dioxol-5-yl)-3-benzyloxy-6-[(1-iminopropyl-3-methoxy)amino]-4H-1-benzopyran-4-one. Yield: 40%; m.p.: 188.5-190.0° C.; TLC (85/25/2/1 Chloroform/Methanol/Water/Ammonia) Rf: 0.54; Elem. anal. $C_{20}H_{18}N_2O_6 \cdot HCl$; theory C, 57.35; H, 4.57; N, 6.69. found C, 56.34; H, 4.5; N, 6.03. $^1$H-NMR ($d_6$-DMSO): 11.4 (s broad, 1H), 9.83 (s broad, 1H), 9.5 (s broad, 1H), 8.75 (s broad, 1H), 8.01-7.87 (m, 4H), 7.75 (dd, 1H); 7.16 (d, 1H); 6.17 (s, 2H), 3.78 (t, 2H), 3.35 (s, 3H), 2.87 (t, 2H).

b) 2-(benzo[1,3]dioxol-5-yl)-3-benzyloxy-6-[(1-iminopropyl-3-methoxy)amino]-4H-1-benzopyran-4-one Prepared analogously to Example 5b) starting from 6-amino-2-(benzo[1,3]dioxol-5-yl)-3-benzyloxy-4H-chromen-4-one and 3-methoxypropyl cyanide, but the obtained hydrochloride was treated with aqueous NaOH, the product was extracted with ethyl acetate, the organic layer washed with water, dried, and evaporated to provide the titled product. Yield: 20%. TLC (9/1 Chloroform/Methanol) Rf: 0.19.

EXAMPLE 20

2-(6-methoxypyridin-3-yl)-3-hydroxy-6-[(1-iminoethyl)amino]-4H-1-benzopyran-4-one

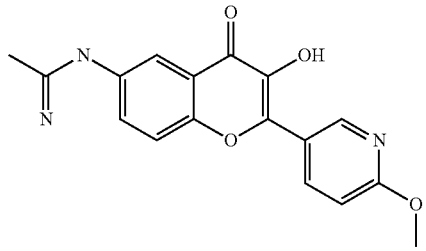 [SMILES: COc1ccc(-c2oc3ccc(NC(C)=N)cc3c(=O)c2O)cn1]

Prepared analogously to Example 5, starting from 2-(6-methoxypyridin-3-yl)-3-benzyloxy-6-[(1-iminoethyl)amino]-4H-1-benzopyran-4-one except that the reaction is carried out without HCl. Yield: 68%; m.p.: 104.5-106.5° C.; TLC (85/25/2/1 Chloroform/Methanol/Water/Ammonia) Rf 0.38; $^1$H-NMR ($d_6$-DMSO): 9.01 (d, 1H), 8.48 (dd, 1H), 7.65 (m, 1H), 7.38-7.19 (m, 2H), 7.04 (m, 1H); 6.4 (s broad, 1H); 3.95 (s, 3H), 1.93 (s, 3H).

b) 2-(6-methoxypyridin-3-yl)-3-benzyloxy-6-[(1-iminoethyl)amino]-4H-1-benzopyran-4-one Prepared analogously to Example 5b), starting from 2-(6-methoxypyridin-3-yl)-3-benzyloxy-6-amino-4H-1-benzopyran-4-one, but the obtained hydrochloride was treated with aqueous NaOH, the product was extracted with ethyl acetate, the organic layer washed with water, dried, and evaporated to provide the titled product. Yield: 43%; TLC (85/25/2/1 Chloroform/Methanol/Water/Ammonia) Rf: 0.69, $^1$H-NMR ($d_6$-DMSO): 8.81 (d, 1H), 8.25 (m, 1H), 7.63 (m, 1H), 7.4-7.1 (m, 6H); 6.97 (d, 1H); 6.39 (m, 1H); 5.11 (s, 2H), 3.94 (s, 3H); 1.99-1.75 (m, 3H).

c) 2-(6-methoxypyridin-3-yl)-3-benzyloxy-6-amino-4H-1-benzopyran-4-one

To a suspension of 2-(6-methoxypyridin-3-yl)-3-benzyloxy-6-(N-tertbutoxycarbonylamino)-4H-1-benzopyran-4- one (0.067 mol) in DCM (90 ml) trifluoroacetic acid (30 ml) was added. The mixture was stirred for 1 hour at r.t. and concentrated. Aqueous NaHCO$_3$ was added and the mixture was extracted with ethyl acetate, washed with water, dried, and concentrated. The solid was suspended in ethyl ether, filtered and dried. Yield: 78%; TLC (9/1 Chloroform/Methanol) Rf: 0.56.

d) 2-(6-methoxypyridin-3-yl)-3-benzyloxy-6-(N-tertbutoxycarbonylamino)-4H-1-benzopyran-4-one Prepared analogously to Example 5d), starting from 2-(6-methoxypyridin-3-yl)-3-hydroxy-6-(N-tertbutoxycarbonylamino)-4H-1-benzopyran-4-one. Yield: 74%; TLC (9/1 Chloroform/Methanol): Rf 0.89, $^1$H-NMR (d$_6$-DMSO): 9.78 (s broad, 1H), 8.81 (d, 1H), 8.31 (d, 1H), 8.25 (dd, 1H); 7.79 (dd, 1H); 7.68 (d, 1H); 7.30 (m, 5H), 6.97 (d, 1H); 5.16 (s, 2H), 3.94 (s, 3H), 1.52 (s, 3H).

e) 2-(6-methoxypyridin-3-yl)-3-hydroxy-6-(N-tert-butoxycarbonylamino)-4H-1-benzopyran-4-one Prepared analogously to Example 5e), (starting from 2-hydroxy-5-amino-N—BOC-acetophenone) except that the work-up was carried out without HCl. Yield: 41%; $^1$H-NMR (d$_6$-DMSO): 9.63 (s broad, 1H), 9.17 (d, 1H), 8.63 (dd, 1H), 8.27 (d, 1H); 7.66 (m, 2H); 6.95 (d, 1H); 3.92 (s, 3H), 1.51 (s, 3H).

f) 2-hydroxy-5-amino-N—BOC-acetophenone

To a suspension of 2-hydroxy-5-amino-acetophenone hydrochloride (0.133 mol) in THF (450 ml), a solution of NaHCO$_3$ (0.332 mol) in water (200 ml) wad added. Ditertbuthyldicarbonate (0.2 mol) was added portion wise at 0° C. and the mixture was stirred for 1 hour at 0° C. and for 16 hours at r.t. THF was evaporated and mixture was extracted with ethyl acetate, washed with water, dried, and concentrated. The obtained solid was suspended in petroleum ether, filtered and dried. Yield: 90%; TLC (2/1 Petroleum ether/Ethyl acetate) Rf: 0.63, Elem. anal. C$_{13}$H$_{17}$NO$_4$; theory C, 62.14; H, 6.82; N, 5.57. found C, 61.6; H, 6.91; N, 5.30. $^1$H-NMR (d$_6$-DMSO): 11.54 (s broad, 1H), 9.28 (s broad, 1H), 8.0 (d, 1H), 7.55 (dd, 1H); 6.9 (d, 1H); 2.59 (s, 3H); 1.48 (s, 9H).

EXAMPLE 21

2-(6-hydroxypyridin-3-yl)-3-hydroxy-6-[(1-iminoethyl)amino]-4H-1-benzopyran-4-one hydrochloride

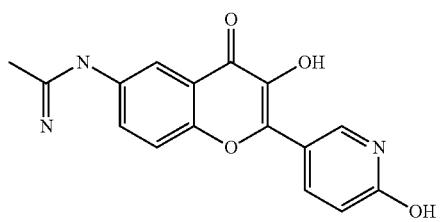 [SMILES: CC(=N)Nc1ccc2oc(-c3ccc(O)nc3)c(O)c(=O)c2c1]

Prepared analogously to Example 5b), starting from 2-(6-hydroxypyridin-3-yl)-3-hydroxy-6-[(1-iminoethyl)amino]-4H-1-benzopyran-4-one hydrochloride. Yield: 45%; m.p.: 284.5-286.0° C. TLC (5/2/2 Buthanol/Acetic acid/Water) Rf: 0.28; Elem. anal. C$_{16}$H$_{13}$N$_3$O$_4$*HCl; theory C, 55.26; H, 4.06; N, 12.08. found C, 54.58; H, 3.79; N, 11.76. $^1$H-NMR (d$_6$-DMSO): 12.28 (s broad, 1H), 11.68 (s broad, 1H), 9.96 (s broad, 1H), 9.65 (s broad, 1H), 8.67 (s broad, 1H), 8.44 (d, 1H), 8.25 (dd, 1H), 8.01-7.91 (m, 2H); 7.69 (dd, 1H); 6.55 (m, 1H), 2.39 (s, 3H). MS (EI): 312 (M+1).

b) 2-(6-hydroxypyridin-3-yl)-3-benzyloxy-6-[(1-iminoethyl)amino]-4H-1-benzopyran-4-one hydrochloride To a suspension of 2-(6-methoxypyridin-3-yl)-3-benzyloxy-6-[(1-iminoethyl)amino]-4H-1-benzopyran-4-one (0.6 g) in ethanol (30 ml) was added HCl 6N (2 ml). The mixture was stirred under reflux for 30 hours, cooled and the hydrochloride was filtered off. Yield: 40%.

EXAMPLE 22

2-[(4-benzyloxy-phenyl]-3-hydroxy-6-[(1-iminoethyl)amino]-4H-1-benzopyran-4-one hydrochloride

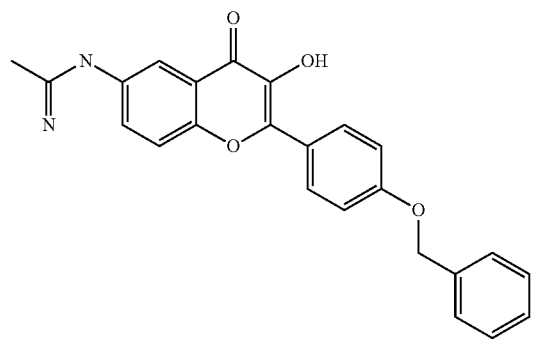 [SMILES: CC(=N)Nc1ccc2oc(-c3ccc(OCc4ccccc4)cc3)c(O)c(=O)c2c1]

Prepared analogously to Example 5b) starting from 2-[(4-benzyloxy-phenyl]-3-hydroxy-6-[(1-iminoethyl)amino]-4H-1-benzopyran-4-one hydrochloride. Yield: 70%; TLC (80/20/2 Chloroform/Methanol/Ammonia) Rf: 0.71; MS (EI) 401 (M+1); IR (KBr): 3423, 3288, 3066, 1677, 1600, 1554, 1395, 1184 cm$^{-1}$; $^1$H-NMR (d$_6$-DMSO): 8.29 (d, 2H), 8.1 (d, 1H), 7.85 (m, 1H), 7.69 (m, 1H), 7.5-7.3 (m, 4H); 7.17 (d, 2H), 5.18 (s, H), 2.46 (s, 3H).

b) 2-[(4-benzyloxy-phenyl]-3-hydroxy-6-amino-4H-1-benzopyran-4-one hydrochloride Prepared analogously to that of Example 5b) starting from 2-[(4-benzyloxy-phenyl]-3-hydroxy-6-acetamido-4H-1-benzopyran-4-one Yield: 85%; TLC (9/1 Chloroform/Methanol) Rf: 0.76; Elem. anal. C$_{22}$H$_{17}$NO$_4$*HCl; theory C, 66.75; H, 4.58; N, 3.54. found C, 66.85; H, 4.22; N, 3.45; $^1$H-NMR (d$_6$-DMSO): 8.20 (d, 2H), 7.8 (m, 2H), 7.65-7.35 (m, 6H), 7.22 (d, 2H), 5.22 (s, 2H).

c) 2-[(4-benzyloxy-phenyl]-3-hydroxy-6-acetamido-4H-1-benzopyran-4-one

Prepared analogously to Example 5d). Yield: 63%; TLC (9/1 Chloroform/Methanol); $^1$H-NMR (d$_6$-DMSO): 10.26 (s broad, 1H), 9.43 (s broad, 1H), 8.43 (d, 1H), 8.20 (d, 2H), 7.90 (dd, 1H), 7.72 (d, 1H), 7.6-7.3 (m, 5H), 7.22 (d, 2H), 5.20 (s, 2H), 2.10 (s, 3H).

Pharmacological Evaluation of the Compounds of the Invention

Arthritis (OA and RA) are characterised by progressive destruction of the cartilage. Aggrecan has been shown to be the main molecular target in this pathology since early destruction of this cartilage component trigger a series of events which give rise to the loss of the articular functionality. Aggrecan molecule consists of several functional and structural domains among them the globular domain G1 seems to play a crucial role, since the G1 domain binds to hyaluronic acid polymers assuring a tight conjunction between the two macromolecules thus providing one of the main crossing points in the complex cartilage architecture. It has been shown how proteolytic cleavage of aggrecan between G1 and G2 globular domains, and in particular at the specific $Glu^{373}$-$Ala^{374}$ bond can destroy the consistency of the aggrecan-hyaluronic acid network, and how aggrecan fragments cleaved at this site can be detected in the synovial fluids of patients with arthritis. Two enzymes ADAMTS-4 and ADAMTS-5, belonging to the ADAMTS family have been identified (Arner et al., J. Biol. Chem. 1999, 274, 10, 6594; Tortorella et al., Science, 1999, 284, 1664) as the main players in the aggrecan cleavage at the $Glu^{373}$-$Ala^{374}$ bond crucial site. Accordingly inhibition of these enzymes should provide therapeutic benefit to diseases such as: osteoarthritis, joint injury, psoriatic arthritis and rheumatoid arthritis.

Several members of the ADAMTS family including ADAMTS-4 and ADAMTS-5 have been found over-expressed in tumour cell lines and these enzymes can be involved in cancer cell migration and angiogenesis. Accordingly, inhibition of these enzymes could prevent cancer invasiveness and tumour progression and should provide therapeutic benefit to diseases such as: brain tumours, in particular glioblastoma, colon cancer, multiple myeloma, breast, cervical, prostate and lung cancer.

The inhibitory effect upon ADAMTS-4 and ADAMTS-5 activity exerted by compounds of formula (I) and their pharmaceutically acceptable salts and solvates thereof has been assessed as described below.

The InviLISA Aggrecanase activity assay (Invitek GmbH, Berlin) was used to screen and characterise aggrecanase inhibitors. The assay was carried out in two steps, according to Will et al. (Will H, Dettloff M, Bendzko P, Svenshnikov P, A Quantitative Assay for aggrecanase Activity; 2005, Journal of Biomolecular Techniques, 16 (4), 459-472). A recombinant fragment of human aggrecan interglobular domain (aggrecan-IGD; $T_{331}$-$G_{458}$) is first digested with aggrecanase. Proteolytic cleavage of the substrate releases an aggrecan peptide with the N-terminal sequence ARGSVIL (ARGSVIL-peptide), that was then quantified with two monoclonal anti-peptide antibodies (ELISA module). For precise calculation of product, ARGSVIL-peptide standard concentrations were run in parallel.

In details:

1) Proteolysis of aggrecan-IGD by aggrecanase. Aggrecan-IGD was incubated with standard recombinant human aggrecanase 1 (ADAMTS-4 aminoacids $F_{213}$-$A_{579}$ with C-terminal tag) or standard recombinant human aggrecanase 2 (ADAMTS-5 aminoacids $S_{262}$-$G_{625}$ with C-terminal tag) in the absence (total enzymatic activity) or presence (modulated enzymatic activity) of inhibitors to be tested. Enzymes were pre-incubated with the inhibitors or the appropriate concentration of diluent as control (DMSO 0.25% final concentration in proteolysis), at 4° C. for 30 min prior to assaying their activity. Five microliters of mix enzyme-inhibitor were added to the substrate (0.1 µM final concentration) in a total volume of 100 µL and incubated for 15 minutes at 37° C. The reaction was terminated with EDTA-containing buffer. The inhibitors were tested at 10 µM final concentration and compounds achieving ≧50% inhibitory effect were evaluated for $IC_{50}$ calculation, in a range generally extended from 0.1 to 10 µM final concentration.

2) Aggrecan peptide ELISA. ARGSVIL-peptide standard, proteolytic digestion of Aggrecan-IGD with standard aggrecanases and test samples were incubated in microtiter wells pre-coated with anti-ARGSVIL-neoepitope antibody. ARGSVIL-peptide is bound to the coated antibody, while other components are removed by washing and aspiration. The bound ARGSVIL-peptide was detected with a second peroxidase-labelled antibody. Any excess of the conjugate was removed by washing and aspiration. The amount of peroxidase bound to different wells was determined in reactions with peroxidase substrate TMB. The reactions are stopped by addition of sulphuric acid solution and absorbance is read at 450 nm in a microtiter plate spectrophotometer.

The aggrecanases inhibitory activity of representative examples of compounds of formula (1) is reported in Table 1.

TABLE 1

| Example | ADAMTS-4 % of inhibition or $IC_{50}$ (µM) | ADAMTS-5 % of inhibition or $IC_{50}$ (µM) |
|---|---|---|
| 1 | 10% | 30% |
| 2 | 30% | 30% |
| 3 | 40% | 10 µM |
| 4 | 40% | 10% |
| 5 | 30% | 0.87 µM |
| 6 | 1.61 µM | 0.20 µM |
| 7 | 31% | 2.4 µM |
| 8 | 10 µM | 10 µM |
| 9 | 20% | 11.5 µM |
| 10 | 0.61 µM | 3.5 µM |
| 11 | 30% | 40% |
| 12 | 2.7 µM | 1.12 µM |
| 13 | 0% | 2.8 µM |
| 14 | 0% | 10 µM |
| 15 | 10% | 15 µM |
| 16 | 32% | 5 µM |
| 17 | 20% | 8 µM |
| 18 | 0% | 4.3 µM |
| 19 | 0% | 8 µM |
| 20 | 0% | 2.2 µM |
| 21 | 10 µM | 20% |
| 22 | 10 µM | 34% |

Arthritis (OA and RA) in addition to lead to loss of joints function are associated with increasing chronic pain during disease progression. Even though arthritis is not the only pathology which can give rise to chronic pain, it is rather common and quite representative of this kind of pain. Chronic pain can be divided into inflammatory pain, a kind of pain more related to peripheral tissue damage/inflammation, and neuropathic pain. Neuropathic pain refers clinically to a group of chronic pain syndromes. Neuropathic pain conditions are the consequence of a number of diseases, for instance diabetes, cancer, amputees, multiple sclerosis. In order to identify effective agents for the clinical management of pain, several alternate pharmacological approaches have been carried out in the last decade, for example COX-2 inhibitors, displayed a good efficacy in the treatment of inflammatory pain, but lacked effectiveness in the treatment of neuropathic pain, in addition for COX-2 inhibitors undesirable life threatening side-effects have been reported.

Independently upon their aggrecanases inhibition properties, compounds of formula (I) have been proved to be potent analgesics in several models of inflammatory, chronic and neuropathic pain.

Accordingly, the compounds of the invention are useful for the treatment of both acute and chronic pain, including but not limited to: postoperative pain, muscular pain, pain resulting from various forms of trauma, as well as chronic pain, neuropathic pain, cancer pain, pain caused by arthritis and visceral pain.

Compounds of the invention are not effective in inhibiting cycloxygenase enzymes (COX-1 and COX-2), since they have been proven not to be effective up to $10^{-5}$ M concentration, in standard in vitro test either for COX-1 or for COX-2 enzyme inhibition.

The efficacy of the compounds of Formula (I) for the treatment of inflammatory and neuropathic pain has been determined using the following in vivo animal models.

The interplantar injection of Zymosan-induced mechanical hyperalgesia was used as a model of inflammatory pain (Meller, Neuropharmacology, 1994, 33, 1471-1478). In this model, typically a male Sprague-Dawley or Wistar rat (200-250 g) receives an interplantar injection of 3 mg/100 µl zymosan into one hind paw. A marked inflammation occurs in this hind paw. Drugs are administered orally for evaluation of efficacy, 30 min. before the inflammatory insult. The hyperalgesia induced by zymosan administration was evaluated using the Randall-Selitto method (Arch. Int. Pharmacodyn., 1957, 111, 409). The quantisation of the analgesic effect is achieved by an analgesimeter, which consists in applying to the inflamed paw an increasing weight (from 130-140 g up to 500 g). The difference in the mechanical pain threshold between the basal value (generally 230-250 g) and the one tolerated by the animals treated with the drug, determined 4 hours after the inflammatory challenge, is defined as mechanical hyperalgesia. Mechanical hyperalgesia is expressed for the compounds of the invention as $ED_{50}$, which is the dose of the administered compound able to increase the pain threshold by 50% in comparison with the group of control animals. The corresponding $ED_{100}$, representing the dose able of reducing of 100% the pain threshold, can be calculated for those cases where there is a linear dose-response relationship. For each test compound, at least three doses were used, with 8 animals per group. Compounds of the invention were tested at 10, 20 and 40 mg/Kg.

The performance of representative compounds of formula (I), in the test described above, is summarised in Table 2, where the activity of the compounds of the invention is compared with the performance in the same test of well known standards. Representative compounds of the invention demonstrated efficacy superior or comparable to the standards. In addition, compounds of the invention did not display ulcerative side effects comparable to the ones displayed by Nimesulide, even at the higher doses tested.

TABLE 2

| Compound | $ED_{50}$ | $ED_{100}$ |
|---|---|---|
| | 4 hrs | |
| | mg/kg; OS | |
| Example 1 | 7.9 | 19 |
| Example 2 | 6.5 | 18 |

TABLE 2-continued

| Compound | $ED_{50}$ | $ED_{100}$ |
|---|---|---|
| | 4 hrs | |
| | mg/kg; OS | |
| Example 3 | 12.0 | 24 |
| Example 4 | 12.0 | 35 |
| Celecoxib | 9.0 | NC |
| Tramadol | 25.7 | NC |
| Nimesulide | 5.0 | NC |

NC: Not Calculable

Analgesic activity of the compounds of formula (I) can be further evaluated in an animal model of pain as the one induced by intra-plantar injection of capsaicin.

Analgesic activity of the compounds of formula (I) can be further evaluated in an animal model of chronic inflammatory pain. Since clinically, inflammatory pain is most often associated with chronic conditions such as arthritis and cancer, where any inflammation or plastic neuronal change in the peripheral and central nervous system would have been occurring for long time, chronic animal paradigms in which the inflammatory insult has had time to induce centrally mediate changes, may result more predictive. Recently, it was shown how the use of Complete Freund's Adjuvant (CFA; *Mycobacterium tuberculosis*) as triggering agent for the inflammatory response along with the use of an appropriate protocol can give rise to a more suitable model. CFA-induced prolonged inflammation has been used extensively in studies of behavioural pain response (K. Walker, Mol Med Today, 1999, 5, 319-321) since it has been considered also suitable for studying involvement of neuronal plasticity in chronic pain (R. Sharif Naeini, Eur. J. Neuroscience, 2005, 22, 8, 2005-2015). Experiments are performed as described in the literature (C. J. Woolf, Br. J. of Pharmacology, 1997, 121, 417-424); 8 rats were used for each group, each product was tested at three doses (3, 10, 30 mg/kg), the products were administered i.p., 24 hours after the interplantar challenge, and the analgesic activity was measured starting from the 24 hours following the challenge.

In Table 3, results obtained in this CFA model, for representative compounds of formula (I) are listed in comparison to Piroxicam, a recognised standard. Analgesic effect was assessed using the same equipment as before described for the Randall-Selitto model, results are reported as maximum percent effect (MPE) which represents the difference (%) in pain threshold between the animals treated with the drug and the controls that received only the vehicle (reduction of the nociceptive effect, due to paw loading with increasing weight, in comparison to controls which received CFA treatment). 100% protection means that the animal treated with the compound and CFA can tolerate the same stimulus (weight) as the control animal which has not received CFA treatment. MPE higher than 100% mean that the animal treated with the compound and CFA can tolerate stimuli (weight) higher than the control animals, which has not received CFA treatment (hypoalgesia). From the MPE data at 0.5 hrs, the doses yielding a protection of 50% ($ED_{50}$) and 100% ($ED_{100}$) have been calculated.

TABLE 3

CFA

| Compound | Dose mg/Kg; IP | MPE 0.5 hrs | MPE 1.5 hrs | MPE 3 hrs | MPE 6 hrs | MPE 24 hrs | $ED_{50}$ 0.5 hrs mg/kg; IP | $ED_{100}$ 0.5 hrs mg/kg; IP |
|---|---|---|---|---|---|---|---|---|
| Example 1 | 3 | 30 | 50 | 40 | NE | NE | 4.86 | 8.06 |
|  | 10 | 62 | 39 | NE | NE | NE |  |  |
|  | 30 | 261 | 190 | 37 | NE | NE |  |  |
| Example 2 | 3 | 91 | 87 | 32 | NE | NE | 1.56 | 3.15 |
|  | 10 | 193 | 105 | 42 | 43 | 38 |  |  |
|  | 30 | 254 | 190 | 146 | 89 | 45 |  |  |
| Piroxicam | 3 | 25 | 40 | NE | NE | NE | 7.65 | 34.33 |
|  | 10 | 46 | 73 | 62 | NE | NE |  |  |
|  | 30 | 102 | 111 | 54 | 24 | 38 |  |  |

NE: Not Effective

The compounds of the invention demonstrated also in this test a pronounced analgesic effect, at doses of 10 and 30 mg/Kg, being the highest dose characterised with a remarkable hypoalgesic effect. At this dose range, the representative compounds are much more effective than Piroxicam, the reference standard.

Painful diabetic neuropathy is one of the most common complications of insulin-dependent diabetes in man; in particular, diabetes can be associated with neuropathic pain which fails to be treated by classical analgesics. Streptozotocin (STZ)-induced diabetes in the rat has been increasingly used as a model of painful diabetic neuropathy to assess the efficacies of potential analgesic agents (C. Courteix, Pain 1993, 53, 81-8). A representative compound of the invention was tested for efficacy in reducing mechanical hyperalgesia associated with STZ-induced diabetes in the rat, according to the experimental model as described by the literature. Diabetes was produced with the injection of a single dose (75 mg/Kg i.p.) of STZ. In the following four weeks after the induction of diabetes the clinical symptoms (weight, body and skin temperature, motility and hyperglycemia) progressively developed by the animals, are strictly monitored.

After four weeks, the scores obtained in diabetic rats to various pain stimuli (in particular mechanical stimuli) were greater than those in normal rats, indicating hyperalgesia. The hyperalgesia induced by diabetes was evaluated using the Randall-Selitto method as above described, and quantitated using the analgesimeter. Also in this case, the difference in the mechanical pain threshold between the basal value (generally 230-250 g) and the one tolerated by the animals treated with the drug, is defined as mechanical hyperalgesia. The compound of the invention was administered i.p. (solution, Tween 80, 10% in saline) at different doses, and mechanical hyperalgesia was measured at the reported time, as maximum percent effect (MPE) which represents the difference (%) in pain threshold between the animals treated with the drug and the controls that received only the vehicle, compared with the weight borne by naïf non-diabetic controls. A 100% protection means that the diabetic animals treated with the compound can tolerate the same stimulus (weight) as the naïf non-diabetic animals. MPE higher than 100% means that the diabetic animal treated with the compound can tolerate stimuli (weight) higher than the control non-diabetic animals (hypoalgesia).

In Table 4, the effect of a representative compound of formula (I), in the above described model of neuropathic pain, is compared with some known pharmacological standards used for the clinical treatment of this pathology. In particular, from the MPE data at 0.5 hrs, the doses yielding a protection of 50% ($ED_{50}$) and 100% ($ED_{100}$) have been calculated.

TABLE 4

Neuropathic Pain

| Compound | Dose mg/Kg; IP | MPE 0.5 hrs | MPE 1.5 hrs | MPE 3 hrs | MPE 6 hrs | ED50 0.5 hrs mg/kg; IP | ED100 0.5 hrs mg/kg; IP |
|---|---|---|---|---|---|---|---|
| Example 1 | 3 | 74 | 25 | NE | NE | 0.56 | 10.45 |
|  | 10 | 109 | 54 | NE | NE |  |  |
|  | 30 | 113 | 39 | 39 | 31 |  |  |
| Gabapentin | 30 | 39 | 41 | NE | NE | NC | NC |
|  | 100 | 55 | 38 | NE | NE |  |  |
|  | 300 | 47 | 36 | NE | NE |  |  |
| Amitriptyline | 3 | 44 | 40 | NE | NE | 3.76 | NC |
|  | 10 | 68 | 77 | NE | NE |  |  |
|  | 30 | 65 | 69 | 23 | NE |  |  |
| Tramadol | 3 | 26 | 53 | NE | NE | 10.92 | NC |
|  | 10 | 58 | 48 | 27 | NE |  |  |
|  | 30 | 54 | 64 | 23 | NE |  |  |
|  | 50 | 81 | 60 | 43 | NE |  |  |

NE: not effective;
NC = not calculable

Example 1, the representative compound of formula 1 demonstrated a high efficacy, especially at the doses of 10 and 30 mg/kg (i.e. protection higher than 100%), with $ED_{50}$ and $ED_{100}$ values lower than 10 mg/kg, as in the Zymosan and CFA tests. Conversely, all of the tested standards exhibited a much lower efficacy, if any, in this paradigm. In fact, $ED_{50}$ value was calculable only for Tramadol and Amitriptyline while $ED_{100}$ was not calculable since no standards were able to completely reverse the hyperalgesic-like effect induced by STZ.

Pharmaceutical Compositions

Compounds of formula (I) can be used in the manufacture of a suitable medication for the therapeutic treatment of arthritis, cancer and pain. Accordingly, appropriate pharmaceutical composition of compounds of formula (I), their pharmaceutically acceptable salts and solvates thereof can be used for the treatment of diseases involving destruction of articular cartilage such as traumatic joint injuries, arthritis including osteoarthritis, rheumatoid arthritis and psoriatic arthritis. Appropriate pharmaceutical composition of compounds of formula (I), their pharmaceutically acceptable salts and solvates thereof can be used for treatment of diseases such as: brain tumours, in particular glioblastoma, colon cancer, multiple myeloma, breast, cervical, prostate and lung cancer.

In addition, appropriate pharmaceutical composition of compounds of formula (I), their pharmaceutically acceptable salts and solvates thereof can be used for treatment of acute and chronic pain, including but not limited to inflammatory pain and associated hyperalgesia and allodynia, osteoarthritis pain, postoperative pain, visceral pain, pain associated with cancer, trigeminal neuralgia, acute herpetic and post herpetic neuralgia, neuropathic pain, diabetic neuropathy.

The compounds of the present invention may be administered orally or parenterally, in a pharmacological effective amount. The term parenteral used herein includes intravenous, intramuscular, subcutaneous, intra-dermal and intra-articular. For all methods of treatment herein discussed for the compounds of formula (I), the daily oral dosage regimen will preferably be from about 0.1 to about 20 mg/Kg of total body weight. It will also be recognised by one of skill in the art that the optimal quantity and spacing of individual dosages of a compound of formula (I) will be determined by the nature and extent of the condition being treated.

In order to use a compound of formula (I) in therapy, it will normally be formulated into a dosage form in accordance with conventional methods of pharmacy and current guidelines and relevant good laboratory and manufacturing practices.

The preferred route of administration for the compounds of this invention is oral. The compounds of formula (I) can be formulated in a wide variety of oral dosage forms, such as capsules, tablets, pills, powders and dispersible granules. Suitable carriers can be one or more substances which may also act as diluents, flavouring agents, solubiliser, lubricants, suspending agents, binders.

Suitable carriers include but are not limited to magnesium carbonate, magnesium stearate, talc, lactose, pectin, dextrin, starch, methylcellulose, sodium carboxymethyl cellulose, cocoa butter and the like. Techniques used to prepare oral formulations are the conventional mixing, granulation and compression or capsules filling. Other forms suitable for oral administration include emulsions, syrups and aqueous solutions. Emulsions can be prepared using emulsifying agents for example lecithin, propylene glycol or sorbitan monooleate. Aqueous solutions can be prepared by dissolving the active component in water and adding suitable colorants, flavours, stabilising agents.

The compounds of the present invention may be formulated for parenteral administration (e.g., by injection or by continuous infusion) as a composition with suitable carriers including aqueous vehicles solutions (i.e.: saline, dextrose) or and/or oily emulsions. The drug product may be presented in unit dose forms, for example in ampoules or pre-filled syringes.

The invention claimed is:
1. A compound represented by formula (I):

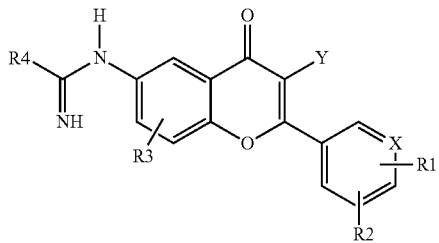

wherein:
X is independently selected from a (—CH—) group or a nitrogen atom (—N—);
Y is independently selected from a hydrogen atom (—H), a hydroxy group (—OH), an alkoxy group (—OR), where R is a $C_1$-$C_4$ linear or branched alkyl chain, or a —OCH$_2$OCH$_3$ group, or a group —O—CH$_2$COOH, or a group —O—CH$_2$COONH$_2$, or a group —O—CH$_2$—COOR, or an alkyl group (—R);

$R_1$ and $R_2$ are independently substituents in the ortho, meta and para positions of the phenyl ring or are independently substituents of the positions: -2, -4, -5 and -6 of the pyridine ring; $R_1$ and $R_2$ substituents are independently selected from: hydrogen (—H), fluorine (—F), chlorine (—Cl), bromine (—Br), $C_1$-$C_4$ linear or branched alkyl chain (—R), trifluoromethyl (—CF$_3$), cyano (—CN), methansulfonyl (—SO$_2$CH$_3$), methansulfonamido (—NHSO$_2$CH$_3$), sulfonamido (—SO$_2$NH$_2$), hydroxy (—OH), alkoxy (—OR), trifluoromethoxy (—OCF$_3$), benzyloxy (—OCH$_2$Ph);

$R_1$ may optionally be a penta-atomic heterocyclic group independently selected from the group consisting of: 1H-1-imidazolyl, 1H-2-methyl-1-imidazolyl, 1H-4-methyl-1-imidazolyl, 1H-5-methyl-1-imidazolyl, imidazol-2-yl, 1-methyl-imidaz-2-yl, oxazol-2-yl, and a group methyl-1H-imidazol-1-yl (—CH$_2$-1H-imidazol-1 yl), wherein when the $R_1$ group is a penta-atomic heterocycle, it may be in position -3 or -4 of the phenyl, or in position -2 and -6 of the pyridine moiety;

when $R_1$ and $R_2$ substituents are in position -3 and -4 of the phenyl, they may optionally form a 5 or 6 member heterocyclic ring condensed with the aryl moiety, said ring independently seclected from the group consisting of a dioxolane, a furane, a 2,3-dihydrofurane and a 1H-3,4-tetrahydropyrane; in these cases, the aromatic group in position -2 of the 4H-1-benzopyrane nucleus is respectively a 1,3-benzodiozol-5-yl group, a benzofuran-5-yl- or benzofuran-6-yl group, a 2,3-dihydrobenzofuran-5-yl or 2,3-dihydrobenzofuran-6-yl group, or a 2,3-dihydro-1,4-benzodioxin-6-yl group;

when $R_3$ is in position -5, -7 or -8 of the 4H-1-benzopyran-4-one nucleus, it is selected from: hydrogen (—H), fluorine (—F), a $C_1$-$C_4$ linear or branched alkyl chain (—R), hydroxy (—OH) methoxy (—OCH$_3$), trifluoromethoxy (—OCF$_3$), carboxy (—COOH), carboalkoxy (—COOR), carboxamido (—CONH$_2$), carboxymethyl (—CH$_2$COOH), carboalkoxymethyl (—CH$_2$COOR), carboxamidomethyl (—CH$_2$CONH$_2$), dimethylaminomethyl (—CH$_2$NMe$_2$);

when the amidino group: $R_4$—C(=NH)—NH—, is in position -6 of the 4H-1-benzopyran-4-one nucleus, $R_4$ is independently selected from a cyclopropyl (—C$_3$H$_5$), a cyclopropylmethyl (—CH$_2$C$_3$H$_5$), a $C_1$-$C_4$ linear or branched alkyl chain (—R), optionally substituted with a hydroxyl group (—OH), a methoxy group (—OCH$_3$), an ethoxy group (—OC$_2$H$_5$) or a dimethylamino group (—NMe$_2$), a phenyl or a substituted phenyl, where said substituted phenyl is a phenyl substituted with at least one of the following groups: fluorine (—F), chlorine (—Cl), bromine (—Br), methoxy (—OCH$_3$) and 3,4-methylendioxy (—O—CH$_2$—O—); in addition, $R_4$ may be a phenyl or a substituted phenyl as defined above or a heterocycle such as—2-furyl, 3-furyl, 2-thienyl, 3-thienyl, 2-oxazolyl, 3-oxazolyl, 2-thiazolyl, 3-thiazolyl; and all the possible tautomers of compounds of formula (I), pharmaceutically acceptable salts thereof, or a solvate or hydrate form of said salts.

2. The compound according to claim 1, wherein the substituent X is a carbon atom and Y is independently selected from a hydrogen atom (—H), or an alkyl group (—R).

3. The compound according to claim 1, wherein the substituent X is a carbon atom and Y is independently selected from an hydroxy group (—OH), an alkoxy group (—OR), a —OCH$_2$OCH$_3$ group, or a group —O—CH$_2$COOH, or a group —O—CH$_2$COONH$_2$, or a group —O—CH$_2$—COOR.

4. The compound according to claim 1, in which the substituent X is a nitrogen atom and Y is independently selected from a hydrogen atom (—H), or an alkyl group (—R).

5. The compound according to claim 1, wherein the substituent X is a nitrogen atom and Y is independently selected from an hydroxy group (—OH), an alkoxy group (—OR), a —OCH$_2$OCH$_3$ group, or a group —O—CH$_2$COOH, or a group —O—CH$_2$COONH$_2$, or a group —O—CH$_2$—COOR.

6. The compound according to claim 1, wherein the substituent X is a (—CH—) group, Y is as defined in claim 1 and R$_1$ and R$_2$ are independently substituents in the ortho, meta and para positions of the phenyl ring and independently selected from: hydrogen (—H), fluorine (—F), chlorine (—Cl), bromine (—Br), C$_1$-C$_4$ linear or branched alkyl chains, trifluoromethyl (—CF$_3$), cyano (—CN), methansulfonyl (—SO$_2$CH$_3$), methansulfonamido (—NHSO$_2$CH$_3$), sulfonamido (—SO$_3$NH$_2$), hydroxy (—OH), alkoxy (—OR), trifluoromethoxy (—OCF$_3$), benzyloxy (—OCH$_2$Ph).

7. The compound according to claim 1, where the substituent X is a (—CH—) group, and R$_1$ may be a penta-atomic heterocyclic group independently selected from the group consisting of: 1H-1-imidazolyl, 1H-2-methyl-1-imidazolyl, 1H-4-methyl-1-imidazolyl, 1H-5-methyl-1-imidazolyl, imidazol-2-yl, 1-methyl-imidazol-2-yl, oxazol-2-yl, and a group —CH$_2$-1H-imidazol-1yl, and when the R$_1$ group is a penta-atomic heterocycle, it can be in position -3 and -4 of the phenyl.

8. The compound according to claim 1, in which the substituent X is a (—CH—) group, and the R$_1$ and R$_2$ substituents are in position -3 and -4 of the phenyl, forming a 5 or 6 member heterocyclic ring condensed with the aryl moiety; wherein said ring is a dioxolane, a furane, a 2,3-dihydrofurane or a 1H-3,4-tetrahydropyrane moiety; in these cases, the aromatic group in position -2 of the 4H-1-benzopyrane nucleus is respectively a 1,3-benzodiozol-5-yl group, a benzofuran-5-yl- or benzofuran-6-yl group, a 2,3-dihydrobenzofuran-5-yl or 2,3-dihydrobenzofuran-6-yl group, a 2,3-dihydro-1,4-benzodioxin-6-yl group.

9. The compound according to claim 1, in which the substituent X is a nitrogen atom, and R$_1$ and R$_2$ are substituents independently in the positions: -2, -4, -5 and 6 of the pyridine ring; R$_1$ and R$_2$ substituents are independently selected from: hydrogen (—H), fluorine (—F), chlorine (—Cl), bromine (—Br), alkyl chain (—R), trifluoromethyl (—CF$_3$), cyano (—CN), hydroxyl (—OH), alkoxy (—OR), trifluoromethoxy (—OCF$_3$), benzyloxy (—OCH$_2$Ph).

10. The compound according to claim 1, wherein the substituent X is a nitrogen atom, and R$_1$ may be a penta-atomic heterocyclic group independently selected from the group consisting of: 1H -1-imidazolyl, 1H-2-methyl-1-imidazolyl, 1H-4-methyl-1-imidazolyl, 1H-5-methyl-1-imidazolyl, imidazol-2-yl, 1-methyl-imidazol-2-yl, oxazol-2-yl, and a group methyl-1H-imidazol-1-yl (—CH$_2$-1H-imidazol-1yl); wherein when the R$_1$ group is a penta-atomic heterocycle, it may be in position -6 of the pyridine ring.

11. The compound according to claim 1, in which the amidino group: R$_4$—C(=NH)—NH—, is in position -6 of the 4H-1-benzopyran-4-one nucleus, wherein R$_4$ is independently selected from a cyclopropyl (—C$_3$H$_5$), a cyclopropylmethyl (—CH$_2$C$_3$H$_5$), a C$_1$-C$_4$ linear or branched alkyl chain, optionally substituted with an hydroxy group (—OH), a methoxy group (—OCH$_3$), an ethoxy group (—OC$_2$H$_5$) or a dimethylamino group (—NMe$_2$), a phenyl or a substituted phenyl, where said substituted phenyl is a phenyl substituted with at least one of the following groups: fluorine (—F), chlorine (—Cl), bromine (—Br), methoxy (—OCH$_3$) and 3,4-methylendioxy (—O—CH$_2$—O—).

12. The compound according to claim 1, in which the amidino group: R$_4$—C(=NH)—NH—, is in position -6 of the 4H-1-benzopyran-4-one nucleus, wherein R$_4$ is independently selected from a phenyl or a substituted phenyl as defined above or a heterocycle selected from the group consisting of—2-furyl, 3-furyl, 2-thienyl, 3-thienyl, 2-oxazolyl, 3-oxazolyl, 2-thiazolyl, 3-thiazolyl.

13. The compound according to claim 1 in the form of a pharmaceutically acceptable salt selected from hydrochloride, hydrobromide, hydrogensulphate, sulphate, maleate, fumarate, oxalate, methanesulphonate, succinate, ascorbate, and tartrate.

14. The compound according to claim 1 in the form of a pharmaceutically acceptable solvate or hydrate.

15. A method for the pharmacological treatment of traumatic joint injuries, or arthritis selected from the group consisting of osteoarthritis, rheumatoid arthritis and psoriatic arthritis, comprising administering, to a subject in need thereof, an effective amount of the compound according to claim 1.

16. A method for the pharmacological treatment of osteoarthritis and rheumatoid arthritis pain, and neuropathic pain and chronic pain comprising administering, to a subject in need thereof, an effective amount of the compound according to claim 1.

17. A pharmaceutical composition comprising, as active substance at least one compound according to claim 1, and further comprising pharmaceutically inactive ingredients selected from the group consisting of vehicles, binders, flavourings, sweeteners, disaggregates, preservatives, humectants and mixtures thereof, and ingredients which facilitate transferral or transmucosal absorption or which permit the controlled release of the active substance over time.

18. A pharmaceutical comoposition comprising, as active substance, at least one compound according to claim 1, for parenteral administration selected from the group consisting of intravenous, intramuscular, subcutaneous, intra-dermal, and intra-articular administration, and further comprising pharmaceutically inactive ingredients selected from the group consisting of aqueous vehicles solutions and/or oily emulsions.

* * * * *